(12) United States Patent
Barenboym et al.

(10) Patent No.: US 12,402,887 B2
(45) Date of Patent: Sep. 2, 2025

(54) DEVICES AND METHODS FOR APPLYING A HEMOSTASIS CLIP ASSEMBLY

(71) Applicant: Conmed Corporation, Largo, FL (US)

(72) Inventors: Michael Barenboym, Boston, MA (US); Doug Sjostrom, Tewksbury, MA (US); Daniel P. Damato, Boston, MA (US)

(73) Assignee: Conmed Corporation, Largo, FL (US)

( * ) Notice: Subject to any disclaimer, the term of this patent is extended or adjusted under 35 U.S.C. 154(b) by 574 days.

(21) Appl. No.: 17/773,840

(22) PCT Filed: Nov. 2, 2020

(86) PCT No.: PCT/US2020/058553
§ 371 (c)(1),
(2) Date: May 2, 2022

(87) PCT Pub. No.: WO2021/087461
PCT Pub. Date: May 6, 2021

(65) Prior Publication Data
US 2023/0059424 A1 Feb. 23, 2023

Related U.S. Application Data

(60) Provisional application No. 62/929,209, filed on Nov. 1, 2019.

(51) Int. Cl.
*A61B 17/128* (2006.01)
*A61B 17/00* (2006.01)
*A61B 17/12* (2006.01)

(52) U.S. Cl.
CPC .... *A61B 17/1285* (2013.01); *A61B 2017/003* (2013.01); *A61B 2017/00367* (2013.01);
(Continued)

(58) Field of Classification Search
CPC .............. A61B 17/1285; A61B 17/122; A61B 2017/00473; A61B 17/1227;
(Continued)

(56) References Cited

U.S. PATENT DOCUMENTS 4,651,737 A 3/1987 Deniega
5,626,607 A 5/1997 Malecki et al.
(Continued)

FOREIGN PATENT DOCUMENTS

CN 102727276 A 10/2012
CN 203539404 U 4/2014
(Continued)

OTHER PUBLICATIONS

International Search Report and Written Opinion for PCT Application No. PCT/US2020/058553, dated May 3, 2021.
(Continued)

*Primary Examiner* — Katherine M Shi
(74) *Attorney, Agent, or Firm* — Troutman Pepper Locke LLP; Scott D. Wofsy; Michael J. Pollack

(57) ABSTRACT

A device for applying a hemostatic clip assembly includes a proximal delivery catheter having a handle assembly and an elongated catheter body defining a longitudinal axis extending distally from the handle assembly, and a distal clip assembly removably connected to a distal end of the catheter body. The distal clip assembly includes a distal clip housing, a jaw assembly and a jaw adapter yoke. The jaw assembly has a pair of jaw members fixed to the distal clip housing by a first pin oriented orthogonally relative to the longitudinal axis. The jaw adapter yoke is operatively connected to the jaw members. The proximal delivery catheter is configured to transmit linear motion along and torsion about the longitudinal axis to at least a portion of the distal clip assembly.

(Continued)

At least one of the jaw members is configured to rotate about the first pin between an open and a closed configuration.

14 Claims, 17 Drawing Sheets

(52) U.S. Cl.
CPC .............. *A61B 2017/00477* (2013.01); *A61B 2017/12004* (2013.01)

(58) Field of Classification Search
CPC  A61B 2017/00477; A61B 2017/12004; A61B 17/00234; A61B 17/10; A61B 2017/00367; A61B 17/128; A61B 17/2909; A61B 2017/2912; A61B 2017/2936; A61B 2017/2931; A61B 2017/2946; A61B 2017/2944; A61B 2017/2902; A61B 2017/2903
See application file for complete search history.

(56) References Cited

U.S. PATENT DOCUMENTS

| | | | |
|---|---|---|---|
| 5,749,881 A | 5/1998 | Sackier et al. |
| 5,766,184 A | 6/1998 | Matsuno et al. |
| 5,766,189 A | 6/1998 | Matsuno |
| 6,464,710 B1 | 10/2002 | Foster |
| 7,094,245 B2 | 8/2006 | Adams et al. |
| 7,452,327 B2 | 11/2008 | Durgin et al. |
| 7,494,461 B2 | 2/2009 | Wells et al. |
| 7,879,052 B2 | 2/2011 | Adams et al. |
| 8,083,668 B2 | 12/2011 | Durgin et al. |
| 8,088,061 B2 | 1/2012 | Wells et al. |
| 8,162,959 B2 | 4/2012 | Cohen et al. |
| 8,444,660 B2 | 5/2013 | Adams et al. |
| 8,545,519 B2 | 10/2013 | Aguirre et al. |
| 8,551,119 B2 | 10/2013 | Kogiso et al. |
| 8,663,247 B2 | 3/2014 | Menn et al. |
| 8,685,048 B2 | 4/2014 | Adams et al. |
| 8,709,027 B2 | 4/2014 | Adams et al. |
| 8,771,293 B2 | 7/2014 | Surti et al. |
| 8,845,658 B2 | 9/2014 | Adams |
| 8,858,588 B2 | 10/2014 | Sigmon, Jr. et al. |
| 8,915,837 B2 | 12/2014 | Wells et al. |
| 8,939,997 B2 | 1/2015 | Martinez et al. |
| 8,974,371 B2 | 3/2015 | Durgin et al. |
| 8,979,891 B2 | 3/2015 | McLawhorn et al. |
| 9,271,731 B2 | 3/2016 | Adams et al. |
| 9,332,988 B2 | 5/2016 | Adams et al. |
| 9,339,270 B2 | 5/2016 | Martinez et al. |
| 9,370,371 B2 | 6/2016 | Durgin et al. |
| 9,375,219 B2 | 6/2016 | Surti et al. |
| 9,445,821 B2 | 9/2016 | Wells et al. |
| 9,480,478 B2 | 11/2016 | Adams |
| 9,743,933 B2 | 8/2017 | Phillips-Hungerford et al. |
| 9,775,590 B2 | 10/2017 | Ryan et al. |
| 9,795,390 B2 | 10/2017 | Jin et al. |
| 9,895,154 B2 | 2/2018 | Cohen et al. |
| 9,955,977 B2 | 5/2018 | Martinez et al. |
| 9,980,725 B2 | 5/2018 | Durgin et al. |
| 9,987,018 B2 | 6/2018 | Surti et al. |
| 10,010,336 B2 | 7/2018 | Martinez et al. |
| 10,143,479 B2 | 12/2018 | Adams et al. |
| 10,154,842 B2 | 12/2018 | Wells et al. |
| 10,166,028 B2 | 1/2019 | Menn et al. |
| 10,172,623 B2 | 1/2019 | Adams et al. |
| 10,172,624 B2 | 1/2019 | Adams et al. |
| 10,307,169 B2 | 6/2019 | Wells et al. |
| 10,335,159 B2 | 7/2019 | Naveed et al. |
| 10,537,314 B2 | 1/2020 | Ryan et al. |
| 10,548,612 B2 | 2/2020 | Martinez et al. |
| 10,575,857 B2 | 3/2020 | King et al. |
| 10,588,635 B2 | 3/2020 | Smith et al. |
| 10,595,877 B2 | 3/2020 | Menn et al. |
| 10,624,642 B2 | 4/2020 | Randhawa |
| 10,646,230 B2 | 5/2020 | Phillips-Hungerford et al. |
| 10,786,254 B2 | 9/2020 | Wells et al. |
| 10,792,046 B2 | 10/2020 | Martinez et al. |
| 10,813,650 B2 | 10/2020 | Surti et al. |
| 10,820,904 B2 | 11/2020 | Ryan et al. |
| 10,835,261 B2 | 11/2020 | Menn et al. |
| 10,905,434 B2 | 2/2021 | Estevez et al. |
| 10,952,725 B2 | 3/2021 | Durgin et al. |
| 10,952,742 B2 | 3/2021 | Lehtinen et al. |
| 10,952,743 B2 | 3/2021 | Adams et al. |
| 11,020,125 B2 | 6/2021 | Randhawa et al. |
| 11,045,194 B2 | 6/2021 | King et al. |
| 11,071,552 B2 | 7/2021 | Saenz Villalobos et al. |
| 11,083,465 B2 | 8/2021 | Ryan et al. |
| 11,129,623 B2 | 9/2021 | Saenz Villalobos et al. |
| 11,129,624 B2 | 9/2021 | Martinez et al. |
| 11,202,637 B2 | 12/2021 | Murray et al. |
| 11,253,259 B2 | 2/2022 | Smith et al. |
| 11,399,835 B2 | 8/2022 | Congdon et al. |
| 11,426,177 B2 | 8/2022 | Congdon et al. |
| 2002/0045909 A1 | 4/2002 | Kimura et al. |
| 2006/0155308 A1 | 7/2006 | Griego |
| 2008/0208217 A1 | 8/2008 | Adams |
| 2008/0306491 A1 | 12/2008 | Cohen et al. |
| 2010/0268254 A1 | 10/2010 | Golden et al. |
| 2012/0065646 A1 | 3/2012 | Phillips-Hungerford et al. |
| 2014/0249551 A1 | 9/2014 | Adams et al. |
| 2014/0257342 A1 | 9/2014 | Adams et al. |
| 2014/0364874 A1 | 12/2014 | Adams |
| 2016/0128698 A1 | 5/2016 | Adams et al. |
| 2016/0143644 A1 | 5/2016 | Adams et al. |
| 2016/0213378 A1 | 7/2016 | Adams et al. |
| 2016/0220260 A1 | 8/2016 | Martinez et al. |
| 2017/0325823 A1 | 11/2017 | Phillips-Hungerford et al. |
| 2018/0049745 A1 | 2/2018 | Randhawa et al. |
| 2018/0085122 A1 | 3/2018 | Ryan et al. |
| 2018/0125497 A1 | 5/2018 | Cohen et al. |
| 2018/0140300 A1* | 5/2018 | Randhawa ............. A61B 17/10 |
| 2018/0193021 A1 | 7/2018 | Martinez et al. |
| 2018/0235608 A1 | 8/2018 | Durgin et al. |
| 2019/0053804 A1 | 2/2019 | Wells et al. |
| 2019/0059905 A1 | 2/2019 | Adams et al. |
| 2019/0083099 A1 | 3/2019 | Adams et al. |
| 2019/0083100 A1 | 3/2019 | Menn et al. |
| 2019/0090883 A1 | 3/2019 | Adams et al. |
| 2019/0150929 A1 | 5/2019 | Gregan et al. |
| 2019/0223875 A1 | 7/2019 | Saenz Villalobos et al. |
| 2019/0247049 A1 | 8/2019 | Wells et al. |
| 2020/0138444 A1 | 5/2020 | Martinez et al. |
| 2020/0146686 A1 | 5/2020 | Haack et al. |
| 2020/0163676 A1 | 5/2020 | Menn et al. |
| 2020/0214707 A1 | 7/2020 | Randhawa |
| 2021/0022747 A1 | 1/2021 | Menn et al. |
| 2022/0175386 A1 | 6/2022 | Martinez et al. |

FOREIGN PATENT DOCUMENTS

| | | |
|---|---|---|
| CN | 103989500 A | 8/2014 |
| CN | 104248461 A | 12/2014 |
| CN | 104546055 A | 4/2015 |
| CN | 204364061 U | 6/2015 |
| CN | 107684448 A | 2/2018 |
| CN | 109009310 A | 12/2018 |
| CN | 109640841 A | 4/2019 |
| CN | 109805977 * | 5/2019 |
| CN | 110141295 A | 8/2019 |
| CN | 209884245 U | 1/2020 |
| EP | 0880913 A2 | 12/1998 |
| EP | 3476307 A1 | 5/2019 |
| EP | 3643255 A1 | 4/2020 |
| EP | 3763298 A1 | 1/2021 |
| WO | 9915089 A1 | 4/1999 |
| WO | 2015176361 A1 | 11/2015 |
| WO | 2016184120 A1 | 11/2016 |
| WO | 2020/186838 A1 | 9/2020 |
| WO | 2021/087461 A2 | 5/2021 |
| WO | 2021/087464 A2 | 5/2021 |

(56) References Cited

FOREIGN PATENT DOCUMENTS

| WO | 2022/076032 A1 | 4/2022 |
| WO | 2022/076033 A1 | 4/2022 |
| WO | 2022/260751 A1 | 12/2022 |

OTHER PUBLICATIONS

International Search Report and Written Opinion for PCT Application No. PCT/US2020/058556, dated Jul. 9, 2021.
International Search Report and Written Opinion for International Patent Application PCT/US2021/030246, dated Sep. 30, 2021.
International Search Report and Written Opinion for International Patent Application PCT/US2021/030263, dated Oct. 11, 2021.
International Search Report and Written Opinion for PCT Application No. PCT/US2022/024654, dated Sep. 20, 2022.
"Plastic Buckles, Snap Hooks, Hooks, Bag buckles, Hooks, Studs, Locks", <https://web.archive.org/web/20190530020338/http://www.umei.com/buckles-plastic/plastic-buckles-3.htm,> May 30, 2019 (May 30, 2019).
Office Action issued of the Canatian Intellectual Property Office, dated Aug. 13, 2024, in corresponding Canadian Application No. 3156896.
China National Intellectual Property Administration, First Office Action issued on Jul. 19, 2024, in corresponding Chinese Patent Application No. 202080083565.4.

\* cited by examiner

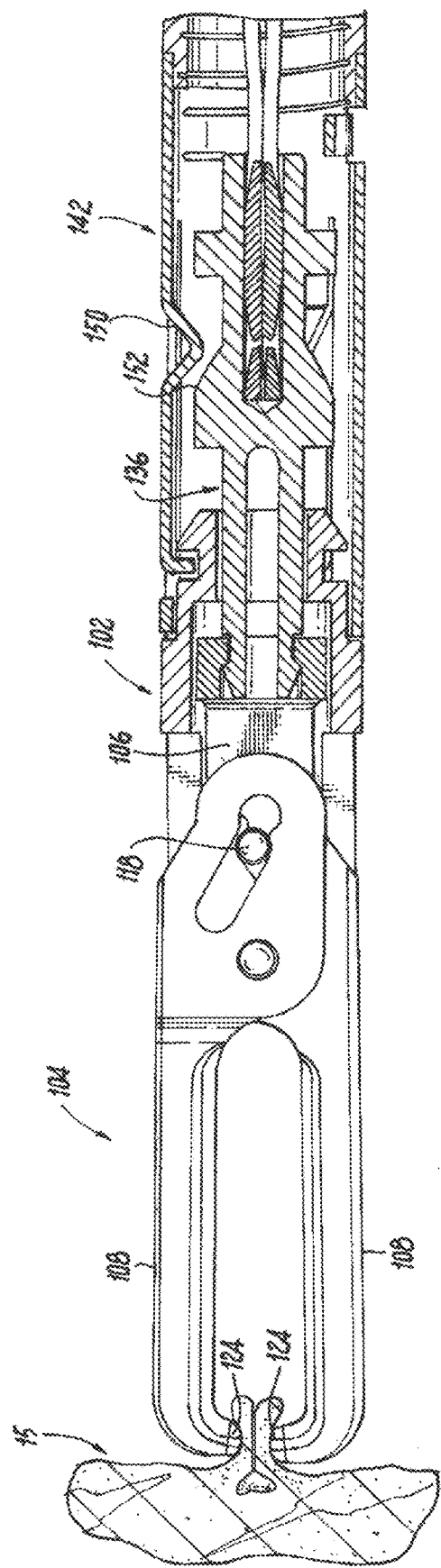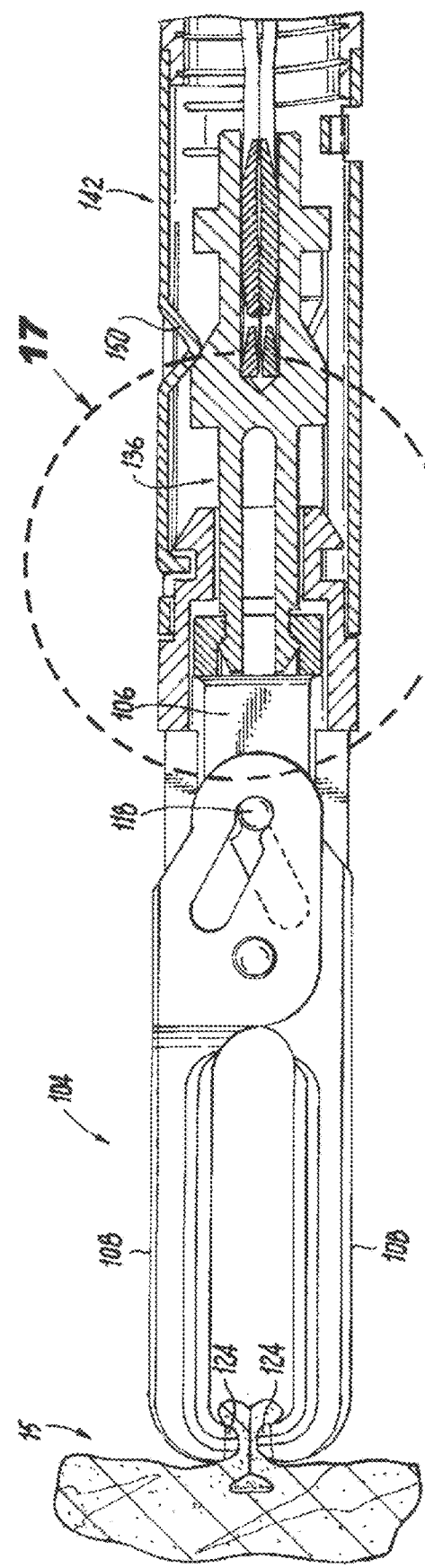

DEVICES AND METHODS FOR APPLYING A HEMOSTASIS CLIP ASSEMBLY

CROSS-REFERENCE TO RELATED APPLICATION

This application is a U.S. National Stage application under 35 U.S.C. 371 of International Application No. PCT/US2020/058553 filed Nov. 2, 2020, which claims the benefit of priority to U.S. Provisional Patent Application Ser. No. 62/929,209 filed Nov. 1, 2019, the disclosure of which is herein incorporated by reference in its entirety.

BACKGROUND OF THE INVENTION

1. Field of the Invention

The subject invention is directed to surgical equipment, and more particularly to hemostatic clips used endoscopic surgical procedures.

2. Description of Related Art

Endoscopic or "minimally invasive" hemostatic clips are used in performance of hemostasis to stop and prevent re-bleeding, or in procedures such as ampullectomies, tissue repair and correction of other tissue defects. Such procedures are typically performed by grasping the tissue with the hemostatic clip. Benefits of using hemostatic clips in such procedures include reduced trauma to the patient, low re-bleeding rate, reduced opportunity for infection, and decreased recovery time.

The subject invention provides an improved mechanism for a hemostatic clip. The novel design allows for a shorter deployed clip body, improved tissue grasping and clip locking, and an improved disconnecting feature, which are described in detail herein below, along with other novel devices and systems.

SUMMARY OF THE DISCLOSURE

The subject invention is directed to a new and useful surgical device for applying a hemostatic clip assembly. The device includes a proximal delivery catheter having a proximal handle assembly and an elongated catheter body extending distally from the proximal handle assembly. The elongated catheter body defines a longitudinal axis. The device includes a distal clip assembly removably connected to a distal end of the elongated catheter body. The distal clip assembly includes a distal clip housing, a jaw assembly and a jaw adapter yoke. The jaw assembly has a pair of cooperating jaw members fixed to the distal clip housing by a first pin. The first pin is oriented orthogonally relative to the longitudinal axis. The jaw adapter yoke is operatively connected to the jaw members. The proximal delivery catheter is configured and adapted to transmit linear motion along the longitudinal axis and torsion about the longitudinal axis to at least a portion of the distal clip assembly. At least one of the jaw members is configured and adapted to rotate about the first pin between an open configuration and a closed configuration.

In accordance with some embodiments, the distal clip housing includes a pair of spaced apart arms defining a slot configured and adapted to provide clearance for respective proximal portions of the jaw members to rotate relative the first pin. The distal clip assembly can include a second pin connecting between the jaw members and the jaw adapter yoke. Each jaw member can include a proximal body portion and a distal end effector. The proximal body portion of each jaw member can include a respective cam slot configured and adapted to receive the second pin and a pivot aperture configured and adapted to receive the first pin.

The second pin can be configured and adapted to translate within the cam slots to move axially relative to the distal clip housing and the jaw assembly to move the jaw members between the open configuration, where respective distal tips of the jaw members are moved away from one another, the closed configuration where the respective distal tips of the jaw members are approximated towards one another to grasp tissue, and a locked configuration.

In some embodiments, each cam slot defines a distal portion and a proximal portion, wherein the distal portion of each cam slot is angled relative to the proximal portion of each cam slot. The proximal portion of each cam slot can define a proximal axis extending in a first direction. The distal portion of each cam slot can define a distal axis extending at an oblique angle relative to the proximal axis, and the distal axes of each cam slot are positioned at opposite angles relative to one another. Each cam slot can include a proximal locking neck projecting into the cam slot defining a proximal locking area. The jaw members can be in the locked configuration when the second pin is proximal relative to the proximal locking neck in the proximal locking area. The proximal locking neck can include at least one of a protrusion projecting into the cam slot or a tapered portion.

The jaw adapter yoke can include a proximal receiving portion and the proximal delivery catheter includes a spring release having a distal portion configured and adapted to be received within the proximal receiving portion of the jaw adapter yoke to transmit axial and rotational force to the jaw adapter yoke. The proximal delivery catheter can include a drive wire coupled to a proximal portion of the spring release to transmit linear and rotational motion from the drive wire to the jaw adapter yoke. The proximal handle assembly can include an actuation portion coupled to a proximal end of the drive wire, and a grasping portion, wherein the actuation portion is configured and adapted to translate relative to the grasping portion to apply axial force to the drive wire.

In certain embodiments, the proximal delivery catheter includes a spring tube between a proximal end of the distal clip assembly and a distal end of the catheter body. The spring tube can include at least one cantilever arm removably coupled to the distal clip housing. The at least one cantilever arm can include an inwardly extending flange that removably engages with a circumferential slot defined about a periphery of a proximal end of the distal clip housing. The proximal delivery catheter can include a spring release positioned at least partially within the spring tube. The spring tube can include an inwardly extending flange portion. The spring release can include an outwardly extending flange portion configured and adapted to interact with the inwardly extending flange portion of the spring tube to selectively deflect the at least one cantilever arm of the spring tube and release the inwardly extending flange of the at least one cantilever arm from the circumferential slot of the distal clip housing.

The spring release can include a distal portion configured and adapted to be received within a receiving portion of the jaw adapter yoke to transmit axial and rotational motion to the jaw adapter yoke. The distal portion of the spring release can be divided into at least two tines. Each tine can have a mating surface selectively engageable with an inner surface of the receiving portion of the jaw adapter yoke. Each tine can be configured and adapted to deflect inwardly and release from the receiving portion when an axial force in a proximal direction is applied to the spring release.

In accordance with another aspect, a device for applying a hemostatic clip assembly includes a proximal delivery catheter including a proximal handle assembly and an elongated catheter body extending distally from the proximal handle assembly. The proximal delivery catheter includes a spring tube positioned at a distal end of the elongated catheter body, a drive wire movably positioned within the elongated catheter body, and a spring release coupled to a distal end of the drive wire, the elongated catheter body defining a longitudinal axis. The spring tube includes an inwardly extending flange portion and the spring release includes an outwardly extending flange portion configured and adapted to interact with the inwardly extending flange portion of the spring tube. The device includes a distal clip assembly removably connected to a distal end of the elongated catheter body. The proximal delivery catheter is configured and adapted to transmit linear motion along the longitudinal axis and torsion about the longitudinal axis to at least a portion of the distal clip assembly.

The distal clip assembly can include a distal clip housing, a jaw assembly having a pair of cooperating jaw members fixed to the distal clip housing by a first pin, and a jaw adapter yoke operatively connected to the jaw members, as previously described. A proximal body portion of each jaw member can include a respective cam slot, like cam slots described above. The distal clip housing can include a pair of spaced apart arms, like those described above. The distal clip assembly can include a second pin like that described above. Each cam slot can include a proximal locking neck projecting into the cam slot defining a proximal locking area, similar to the proximal locking neck and proximal locking area described above. Each cam slot can define a distal portion and a proximal portion, as previously described. The proximal handle assembly can include an actuation portion and a grasping portion, as described above.

In accordance with another aspect, a method for firing a hemostatic clip assembly includes positioning a distal clip assembly proximate to a target location and translating an actuation portion of a proximal handle assembly of a proximal delivery catheter relative to a grasping portion of the proximal handle assembly in at least one of a proximal direction or a distal direction. The distal clip assembly includes a distal clip housing, a jaw assembly having a pair of cooperating jaw members fixed to the distal clip housing by a first pin, and a jaw adapter yoke operatively connected to the jaw members. The proximal delivery catheter includes an elongated catheter body extending distally from the proximal handle assembly. The elongated catheter body defining a longitudinal axis. The actuation portion is operatively connected to the jaw adapter yoke via a drive wire and a spring release to transmit linear motion along the longitudinal axis and torsion about the longitudinal axis to the jaw adapter yoke. The linear motion of the jaw adapter yoke transmits the linear motion to a second pin positioned within a cam slot of at least one jaw member, thereby rotating at least one of the jaw members about the first pin between an open configuration and a closed configuration.

Translating the actuation portion can include translating the actuation portion in the proximal direction to transmit the linear motion in the proximal direction to the second pin to lock the second pin behind a lock protrusion of the cam slot to lock at least one of the jaw members in a locked configuration. Translating the actuation portion can include translating the actuation portion further in the proximal direction to transmit further linear motion in the proximal direction to the spring release. The further linear motion in a proximal direction can de-couple a distal portion of the spring release from a receiving portion of the jaw adapter yoke.

In some embodiments, further linear motion of the spring release in the proximal direction causing abutting between an inner diameter surface of at least one cantilever arm of a spring tube with an outwardly extending flange portion of the spring release. The spring tube can be coupled to a proximal end of the distal clip housing via the at least one cantilever arm. In certain embodiments, the abutting causes the at least one cantilever arm to deflect radially outward and disengage from the proximal end of the distal clip housing.

In accordance with another aspect, a hemostatic clip assembly includes a distal clip housing defining a longitudinal axis, a jaw assembly having a pair of cooperating jaw members fixed to the distal clip housing by a first pin, and a jaw adapter yoke operatively connected to the jaw members. The jaw adapter yoke is configured and adapted to translate axially along the longitudinal axis and rotate about the longitudinal axis. At least one of the jaw members is configured and adapted to rotate about the first pin between an open configuration and a closed configuration. The first pin is oriented orthogonally relative to the longitudinal axis; and The distal clip housing can include a pair of spaced apart arms, similar to those described above. The hemostatic clip assembly can include a second pin, similar to that described above. Each jaw member and its respective cam slot can be similar to those described above.

These and other features of a surgical device for applying a hemostatic clip assembly in accordance with the subject invention will become more readily apparent to those having ordinary skill in the art to which the subject invention appertains from the detailed description of the preferred embodiments taken in conjunction with the following brief description of the drawings.

BRIEF DESCRIPTION OF THE DRAWINGS

So that those skilled in the art will readily understand how to make and use the gas circulation system of the subject invention without undue experimentation, preferred embodiments thereof will be described in detail herein below with reference to the figures wherein:

FIG. 15 is a cross-sectional side elevation view of a portion of the device of FIG. 1, showing the jaw members in the closed configuration where the respective distal tips of the jaw members are approximated towards one another to grasp tissue;

FIG. 16 is a cross-sectional side elevation view of a portion of the device of FIG. 1, showing the jaw members in the locked configuration where the second pin is proximal relative to a proximal locking neck;

DETAILED DESCRIPTION OF THE PREFERRED EMBODIMENTS

Figure 1:
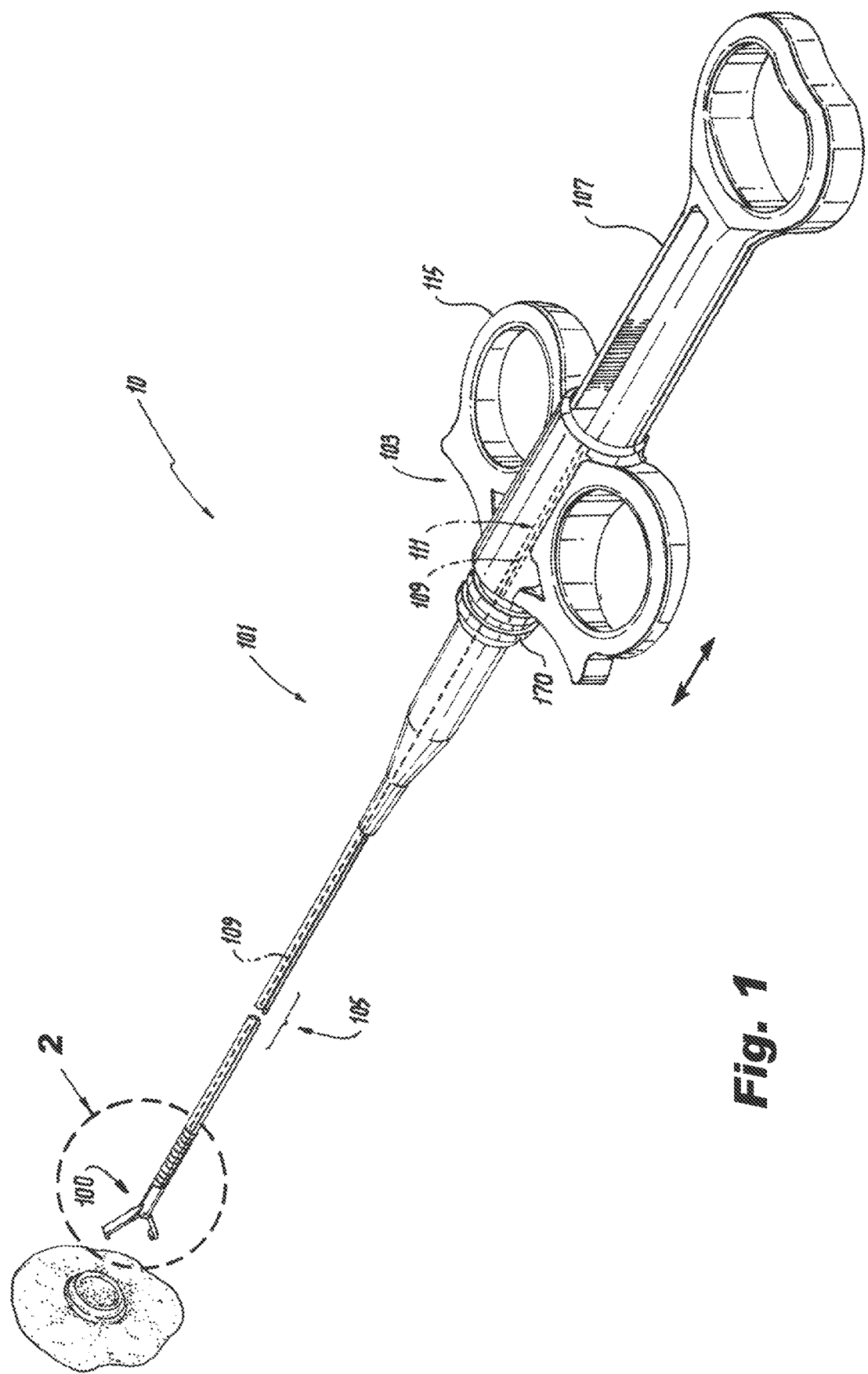
FIG. 1 is a perspective view from the proximal direction of a device for applying a hemostatic clip assembly constructed in accordance with an embodiment of the present disclosure, showing a proximal delivery catheter having a proximal handle assembly and an elongated catheter body and the distal clip assembly.

Referring now to the drawings wherein like reference numerals identify similar structural elements and features of the subject invention, there is illustrated in FIG. 1 a surgical device for applying a hemostatic clip assembly in a patient, and more particularly, for separating the hemostatic clip assembly to function as a short-term implant constructed in accordance with a preferred embodiment of the subject disclosure and is designated generally by reference numeral 10.

Figure 2:
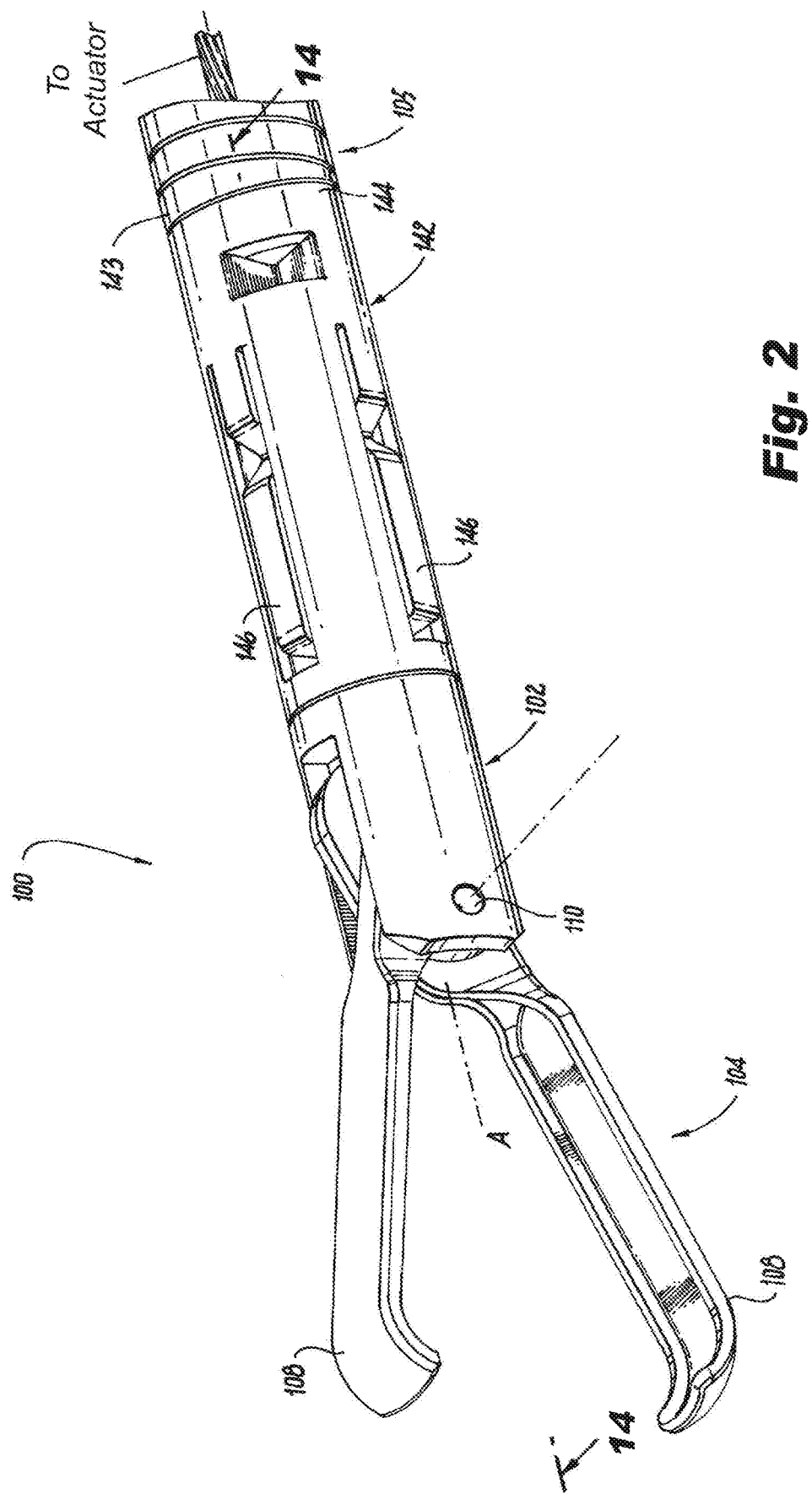
FIG. 2 is a perspective view of the distal clip assembly of FIG. 1, showing a jaw assembly with a pair of cooperating jaw members fixed to the distal clip housing by a first pin.

As shown in FIGS. 1-2, a surgical device 10 for applying a hemostatic clip assembly 100 includes proximal delivery catheter 101 and the distal clip assembly 100. The distal clip assembly 100, e.g., a hemostasis clip, separates from the delivery catheter 101 to function as a short-term implant to stop and prevent re-bleeding, or in procedures such as ampullectomies, tissue repair and correction of other tissue defects. Such procedures are typically performed by grasping the tissue with the hemostatic clip. Using hemostatic clips in such procedures can result in benefits such as reduced trauma to the patient, low re-bleeding rate, reduced opportunity for infection, and decreased recovery time.

With continued reference to FIGS. 1-2, the proximal delivery catheter 101 has a proximal handle assembly 103 and an elongated catheter body 105 extending distally from the proximal handle assembly 103. The elongated catheter body 105 defines a longitudinal axis A. The proximal handle assembly 103 includes an actuation portion 115 (e.g., actuator, as labeled in FIG. 2) coupled to a proximal end 111 of the drive wire 109, and a grasping portion 107. The actuation portion 115 is configured and adapted to translate relative to the grasping portion 107 to apply an axial force to the drive wire 109. Grasping portion 107 and actuation portion 115 are configured and adapted to rotate relative to a cap 170 and catheter body 105, thereby also rotating drive wire 109. Internal annular slots on the distal portion of grasping portion 107 interact with annular tabs on inside diameter of end cap 170 to prevent axial motion of actuation portion 115 and grasping portion but allow rotation.

With continued reference to FIGS. 1-2, the proximal delivery catheter 101 includes a spring tube 142 between a proximal end of the distal clip assembly 100 and a distal end 143 of the catheter body 105. A proximal end 144 of the spring tube 142 is coupled to the distal end 143 of the catheter body via weld, adhesive, or other means. The distal clip assembly 100 includes a distal clip housing 102 and a jaw assembly 104 pivotally connected to the distal clip housing 102. The jaw assembly 104 has a pair of cooperating jaw members 108 fixed to the distal clip housing 102 by a first pin 110. The first pin 110 is oriented orthogonally relative to the longitudinal axis A. The spring tube 142 includes cantilever arms 146 configured and adapted to be removably coupled to the distal clip housing 102, described in more detail below. The hemostatic clip assembly 100 is removably connected to a distal end 143 of the elongated catheter body 105 via the spring tube 142. The proximal delivery catheter 101 is configured and adapted to transmit linear motion along the longitudinal axis A and torsion about the longitudinal axis A to at least a portion of the distal clip assembly 100.

Figure 3:
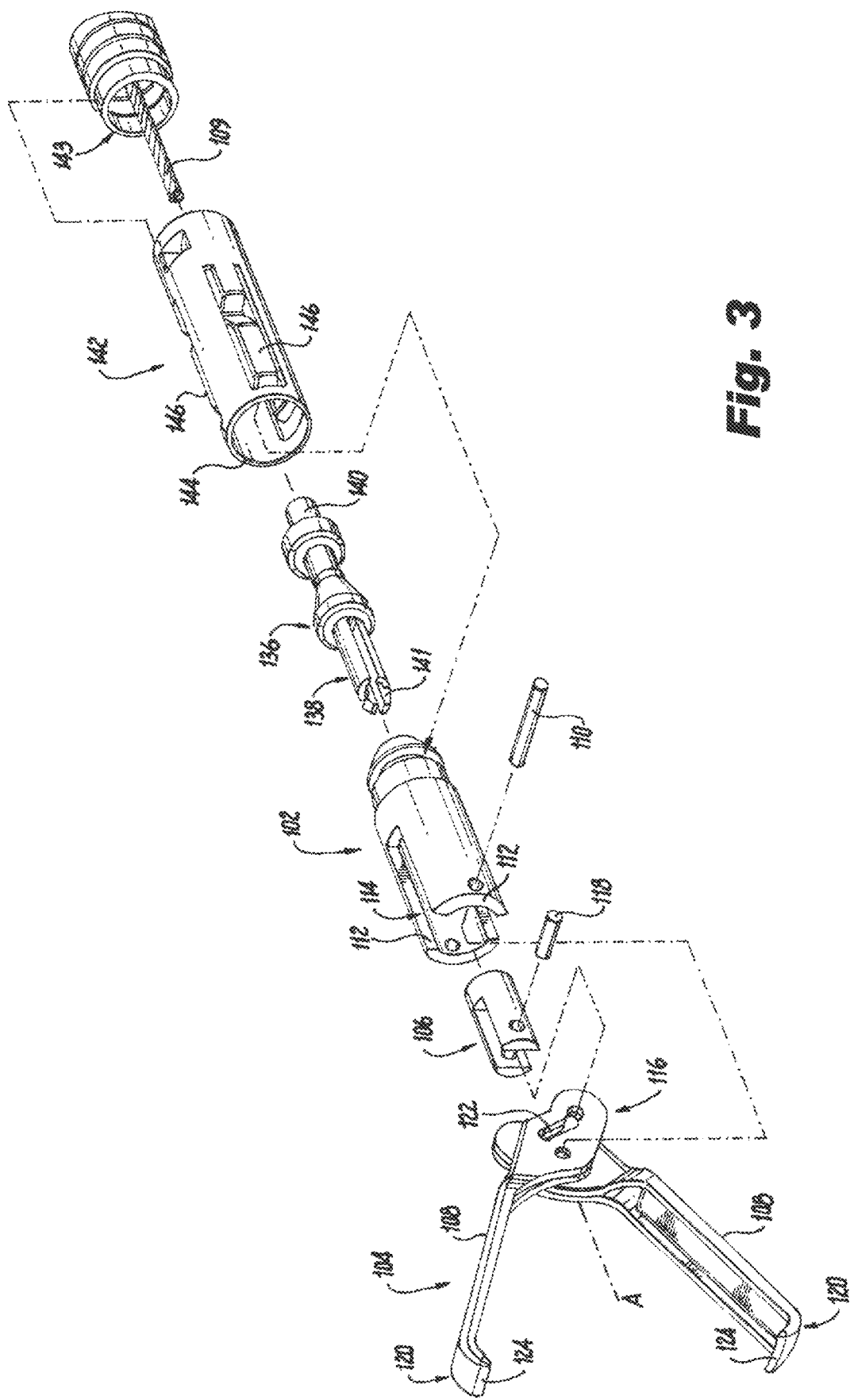
FIG. 3 is an exploded perspective view of a portion of the device of FIG. 1, showing the showing the distal end of the proximal delivery catheter and the distal clip assembly.

With reference now to FIGS. 2-3, the distal clip assembly 100 includes a jaw adapter yoke 106. The proximal delivery catheter 101 includes a spring release 136 having a distal portion 138 configured and adapted to be received within the jaw adapter yoke 106. The distal clip assembly 100 includes a second pin 118 connecting between the jaw members 108 and the jaw adapter yoke 106. The jaw members 108 are configured and adapted to rotate about the first pin 110 between an open configuration and a closed configuration. Each jaw member 108 includes a proximal body portion 116 and a distal end effector 120. The proximal body portion 116 of each jaw member 108 includes a respective cam slot 122 configured and adapted to receive the second pin 118. Jaw members 108 are driven by the second pin 118, e.g., a cam pin, moving along the cam slots 122 of the jaw members 108. The second pin 118 is configured and adapted to translate within the cam slots to move axially relative to the distal clip housing 102 and the jaw assembly 104 to move the jaw members 108 between the open configuration where respective distal tips 124 of the jaw members 108 are moved away from one another, the closed configuration where the respective distal tips 124 of the jaw members 108 are approximated towards one another to grasp tissue, and a locked configuration.

Figure 4:
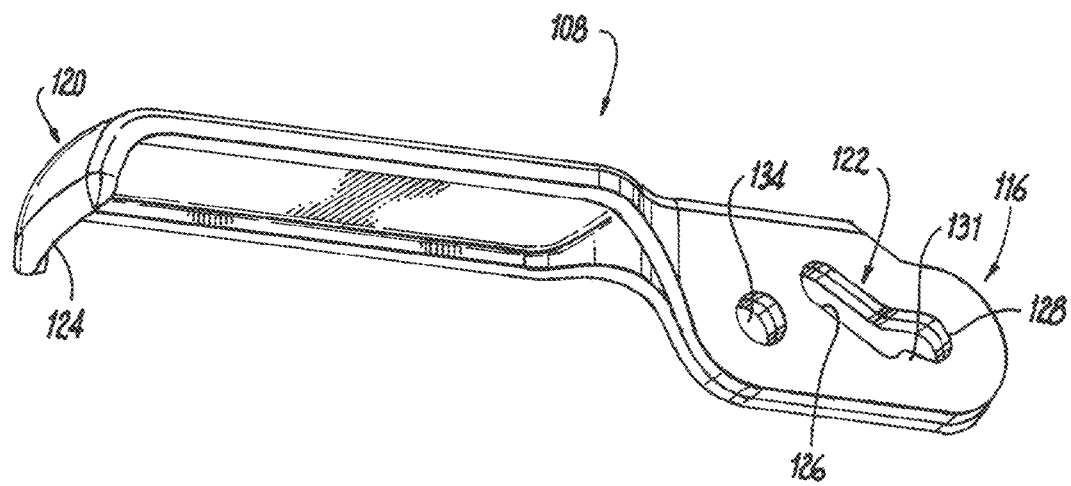
FIG. 4 is a perspective view of a jaw member of the device of FIG. 1, showing the cam slot.
Figure 5:
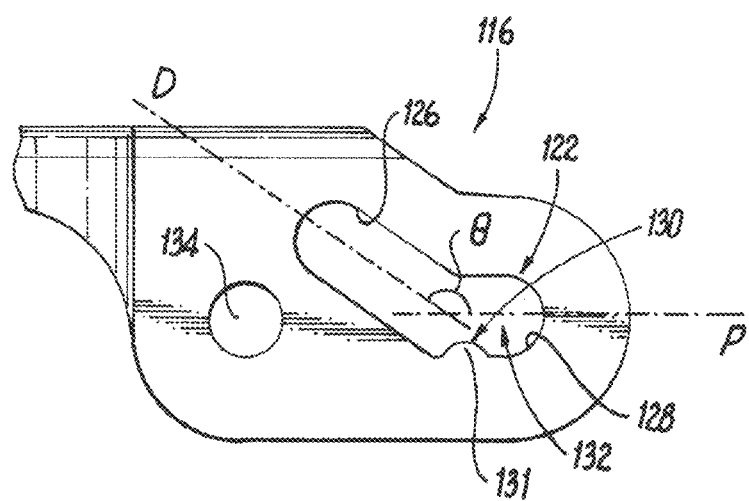
FIG. 5 is a side elevation view of a proximal portion of the jaw member of FIG. 4, showing proximal and distal portions of the cam slot.
Figure 14:
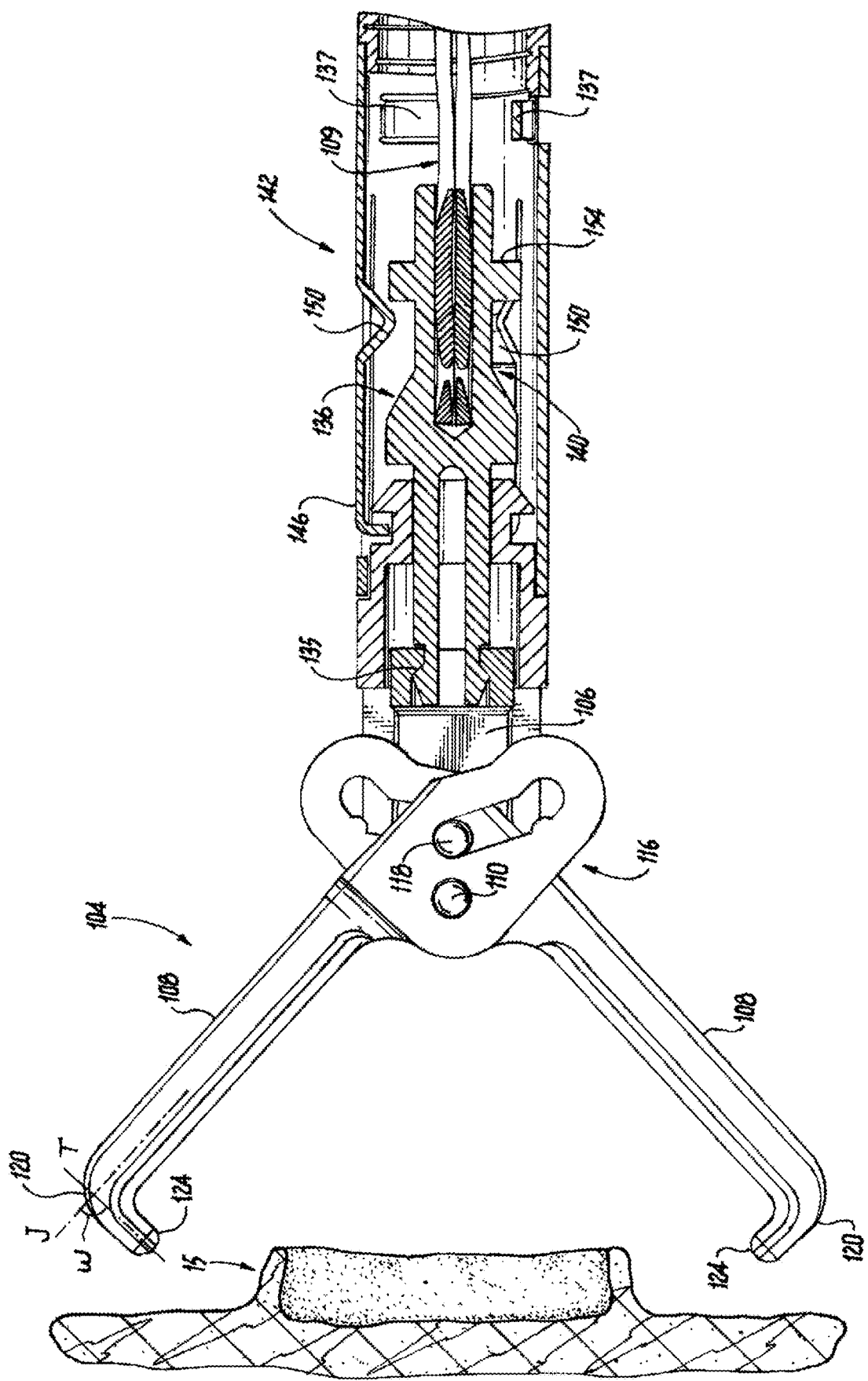
FIG. 14 is a cross-sectional side elevation view of a portion of the device of FIG. 1, showing the jaw members in the open configuration where respective distal tips of the jaw members are moved away from one another to grasp a target area of tissue.

With reference now to FIGS. 3-5, each jaw member 108 includes a pivot aperture 134 configured and adapted to receive the first pin 110. Each jaw member 108 of the jaw assembly 104 is identical to the other member 108, allowing additional economy of scale. The distal end effectors 120 of each jaw member 108 can include at least one pointed peak, multiple peaks, of different or similar size at their distal tips 124. Distal end effectors 120 could also terminate in a combination of pointed peaks and rounded peaks to balance tissue pressure, allowing jaw members 108 to hook tissue with at least one peak and provide atraumatic contact with at least one peak. As shown in FIG. 14, the tooth (or teeth, peaks, etc.) may create an angle ω relative to an axis J of their respective jaw arms 108 between zero and 180 degrees, optimizing the approach angle of distal tips 124 relative to tissue surface. In the embodiment of FIG. 14, the angle ω of a tip axis T relative to axis J is approximately 90 degrees. It is contemplated, however, that the angle ω could be at 0 degrees, such that the tip simply extends from axis J, it could be at 45 degrees, or 180 degrees, where the tip is hooked around such that the tip axis T direction is parallel to axis J. The angle and design of jaw members 108 will be optimized for single jaw tissue retention force during manipulation or tissue apposition. The distance between the pivot aperture 134 and the cam slot 122 dictate the moment arm that translates axial translation to jaw rotation/actuation.

As shown in FIGS. 4-5, each cam slot 122 defines a distal portion 126 and a proximal portion 128, wherein the distal portion 126 of each cam slot 122 is angled relative to the proximal portion 128 of each cam slot 122. The proximal portion 128 of each cam slot 122 defines a proximal axis P extending in a first direction. The distal portion 126 of each cam slot 122 defines a distal axis D extending at an oblique angle θ relative to the proximal axis P, and the distal axes D of each cam slot 122 are positioned at opposite angles relative to one another, as shown in FIGS. 14-16. The angle of a respective distal axis D relative to proximal axis P can be fine-tuned to provide optimal tissue clamping force given a user's maximum acceptable input force.

With continued reference to FIGS. 4-5, Each cam slot 122 includes a proximal locking neck 130, e.g., a locking feature, projecting into the cam slot 122 defining a proximal locking area 132. The jaw members 108 are in the locked configuration when the second pin 118 is proximal relative to the proximal locking neck 130 in the proximal locking area 132. The proximal locking neck 130 includes a protrusion 131 projecting into the cam slot 122. Lock protrusion 131, e.g., a detent, creates a narrowing of cam slot 122 to form the proximal locking neck 130 that interferes with the outer diameter of the second pin 118 as it moves axially in the proximal direction. The continued axial translation of pin 118 forces a widening of the cam slot 122 in an elastic manner and creates an additional resistance force on the internal drivetrain, e.g., spring release 136 and spring tube 142. Once the second pin 118 crests the inflection point on the protrusion 131, it will snap into place behind the protrusion 131, effectively locking the jaws in a closed position. The shape of lock protrusion can vary and can be an arcuate, triangular, or slanted feature. Lock protrusion 131 may also be achieved by reversing the slope of cam slot 122 such that it inflects passed the 0 degree orientation with respect to the axis A of the catheter, described in more detail below. Various embodiments for the proximal locking neck are described below in FIGS. 25-29.

Figure 6:
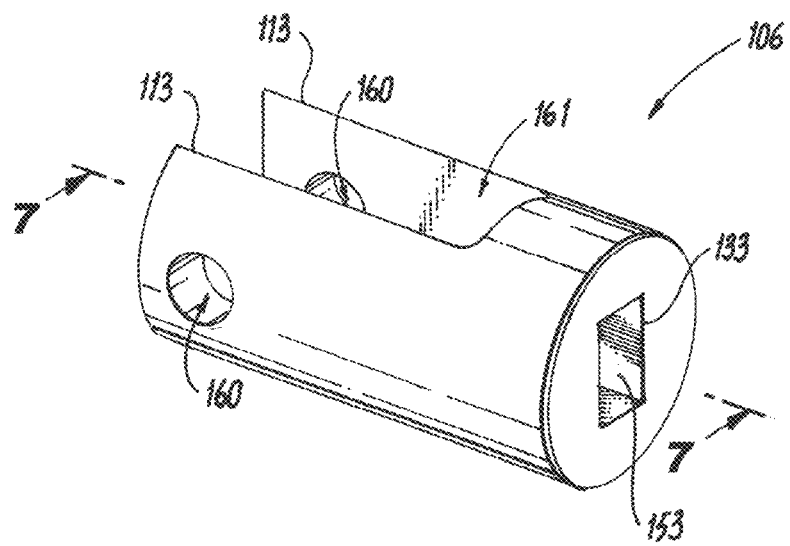
FIG. 6 is a perspective view of a jaw adapter yoke of the device of FIG. 1 from a proximal direction, showing the a proximal receiving portion of the jaw adapter yoke.
Figure 7:
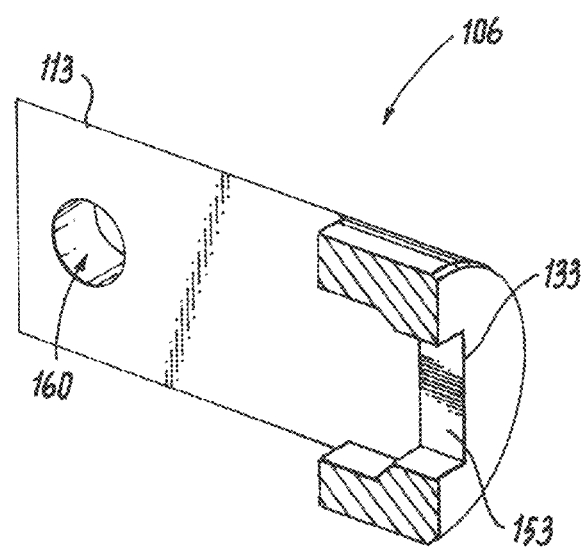
FIG. 7 is a cross-sectional perspective view of the jaw adapter yoke of FIG. 6, showing an inner surface of the proximal receiving portion.

As shown in FIGS. 3 and 6-7, the jaw adapter yoke 106 includes a pin aperture 160 and is operatively connected to the jaw members 108 via second pin 118. The jaw adapter yoke 106 is circular component with two arms 113 extending towards the distal end of the yoke 106 that form a slot 161 therebetween. The slot 161 allows the proximal portions 116 of the jaw members 108 rotate around first pin 110. An aperture 160 is formed in each arm 113 and is in a transverse direction to a longitudinal axis of the jaw adapter yoke and the longitudinal axis A of the catheter body 105. The apertures 160 receive the second pin 118 and can be assembled using orbital riveting or laser tack welding. The jaw adapter yoke 106 includes a proximal receiving portion 133 and slides linearly inside of distal clip housing 102 to drive second pin 118 along the cam slots 122. The proximal receiving portion 133 of the jaw adapter yoke 106 has a square and/or rectangular shape with flat surfaces 153 to mate with a snap feature 141 (described below) on the distal portion 138 of spring release 136, allowing linear force transmission up to a predetermined value.

In certain embodiments, it is contemplated that flat features could be machined onto the back proximal face of the jaw adapter yoke 106, i.e. a transverse slot bisecting the yoke to form bosses that interface with flat faces on the tines of spring release 136, which is shown by embodiments of spring release 736 and yoke 706, shown in FIG. 24 and described below. In some embodiments, the proximal receiving portion 133, e.g., the rectangular hole, could be circular in cross section where an arcuate neck surface 157 on spring release 136 could be in an interference fit with the circular receiving portion such that friction and radial loading would transmit torque between spring release 136 jaw adapter yoke 106.

Figure 8:
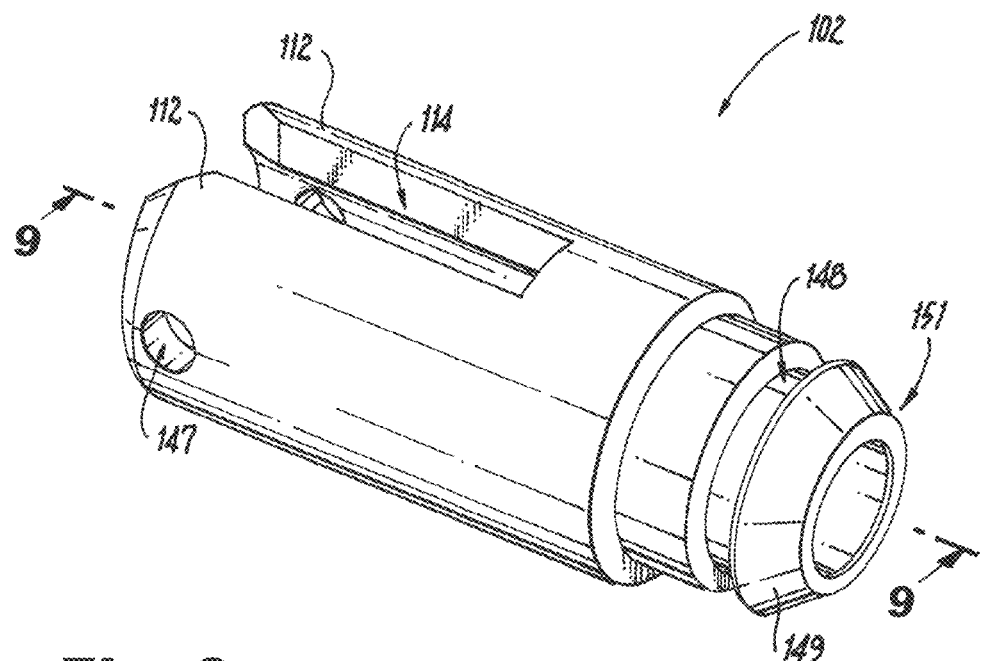
FIG. 8 is a perspective view of a distal clip housing of the device of FIG. 1 from a proximal direction, showing the circumferential slot defined about the periphery of a proximal end of the distal clip housing.
Figure 9:
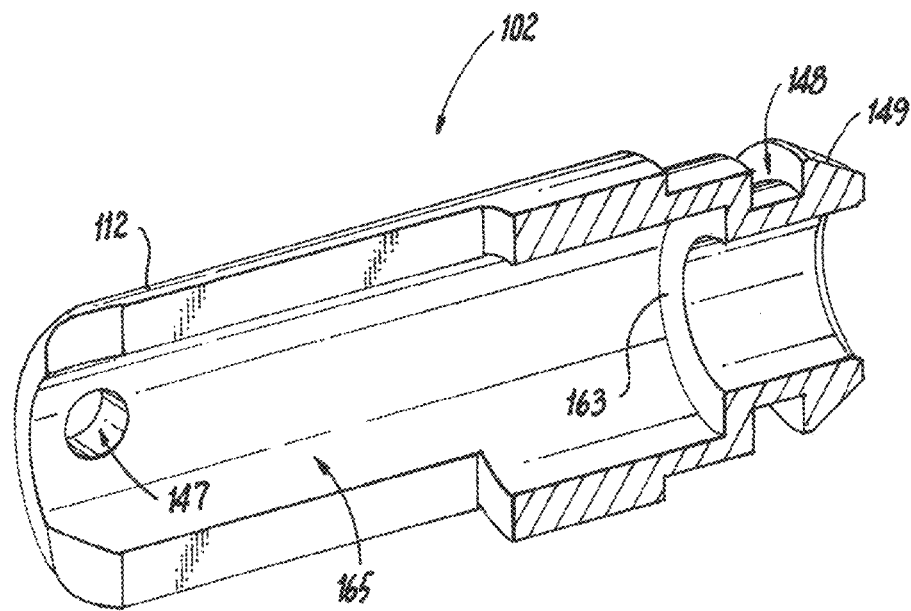
FIG. 9 is a cross-sectional perspective view of the distal clip housing of FIG. 8; showing a distal facing stop surface.
Figures 10, 11:
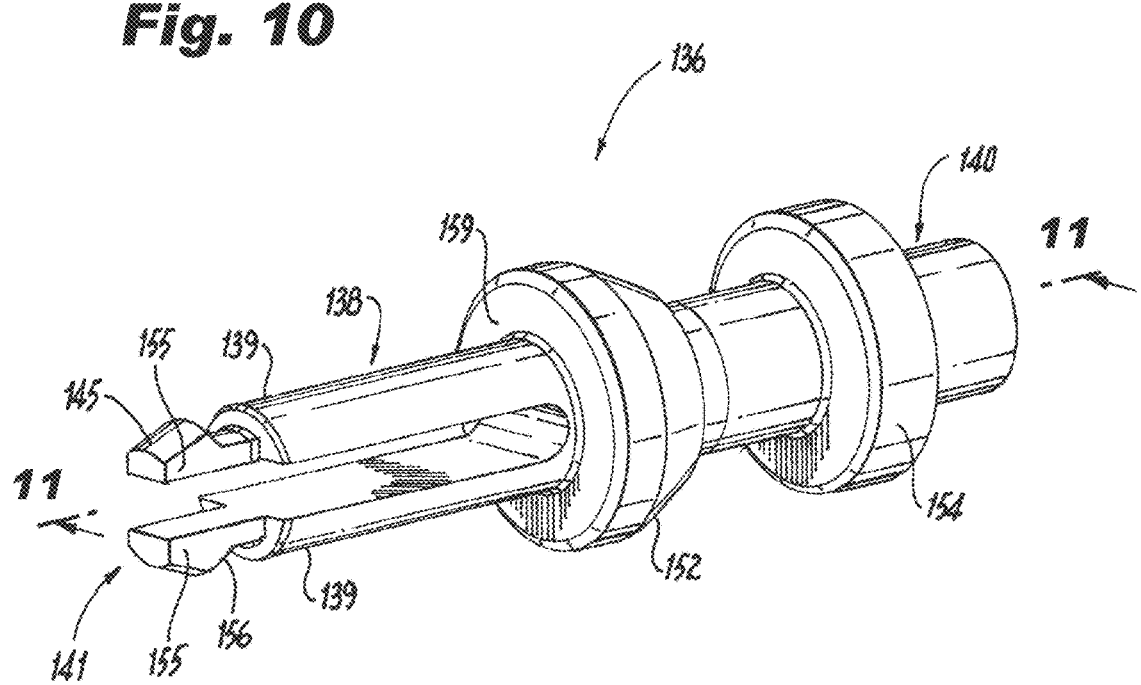
FIG. 10 is a perspective view of a spring release of the device of FIG. 1 from a distal direction, showing a distal portion of the spring release.
FIG. 11 is a cross-sectional side elevation view of the spring release of FIG. 10; showing the mating surfaces of the tines of the distal portion of the spring release.
Figure 12:
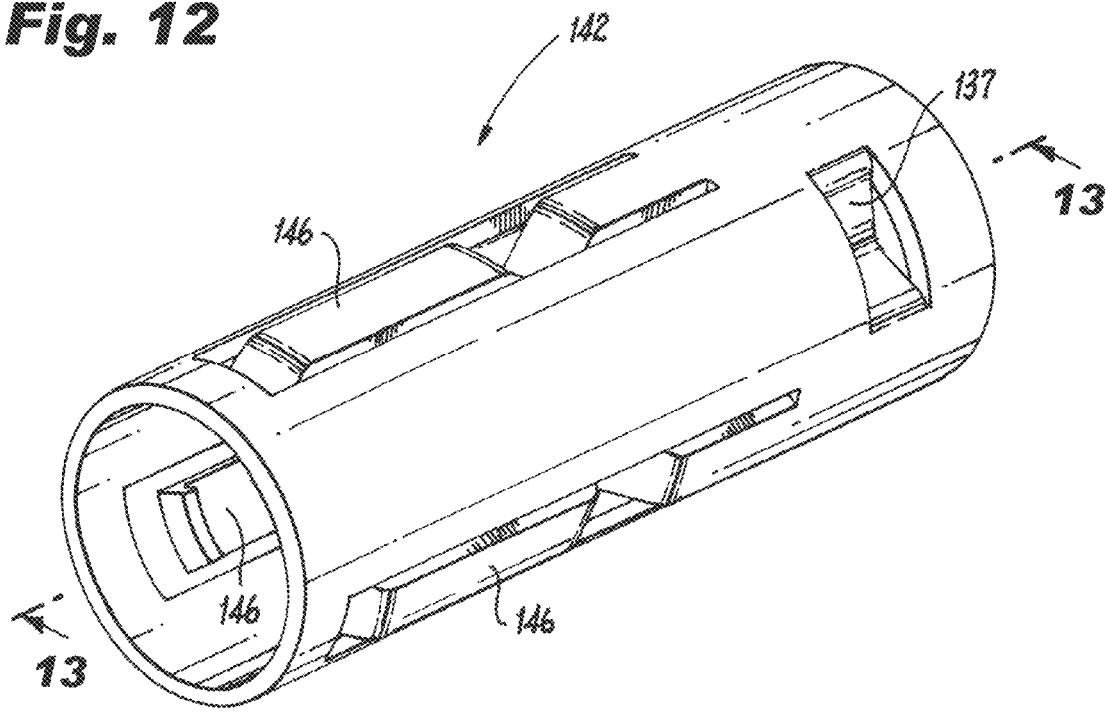
FIG. 12 is a perspective view of a spring tube of the device of FIG. 1 from a distal direction, showing cantilever arms of the spring tube.
Figure 13:
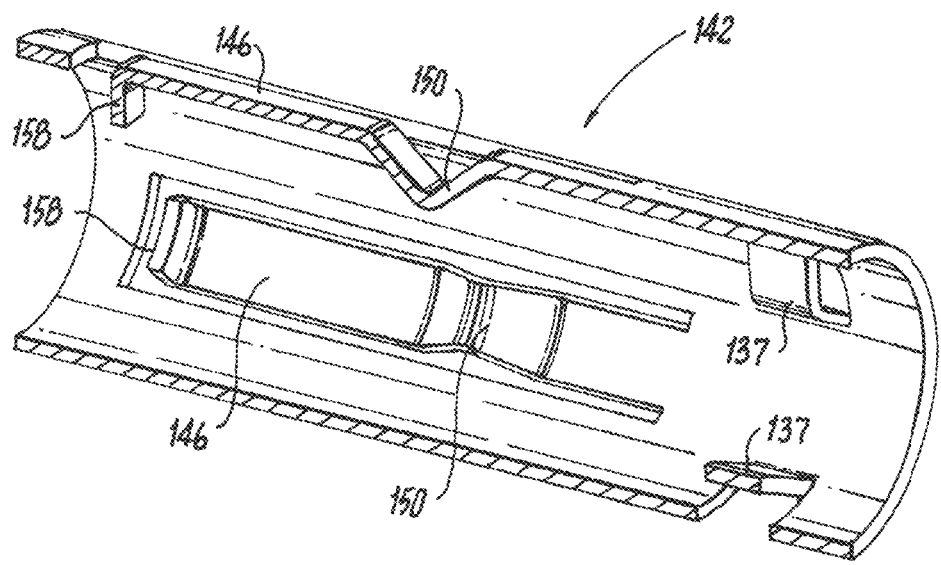
FIG. 13 is a cross-sectional perspective view of the spring tube of FIG. 12, showing inwardly extending flanges of the cantilever arms.

As shown in FIGS. 3 and 8-9, the distal clip housing 102 includes a pair of spaced apart arms 112 defining a slot 114 configured and adapted to provide clearance for respective proximal portions 116 of the jaw members 108 to rotate relative the first pin 110. The distal clip housing 102 connects via a snap fit connection to the spring tube 142 via a circumferential slot 148, e.g., a stepped retention ring, defined about a periphery of a proximal end 151 of the distal clip housing 102. The distal clip housing 102 includes a tapered outer diameter portion 149 proximal relative to the circumferential slot 148. During assembly of the distal clip assembly 100 to the proximal delivery catheter 101, the tapered outer diameter portion 149 pushes the cantilever arms 146 of the spring tube 142 radially outward allowing the 90 degree bent tabs (e.g., the inwardly extending flanges 158 described in more detail below) to seat in the circumferential slot 148 of distal clip housing 102. The distal clip housing 102 includes a transverse hole 147 oriented perpendicular to the longitudinal axis A to accept the first pin 110, e.g., the pivot pin, which couples to jaw members 108. An inner surface 165 of distal clip housing 102 further includes a distal facing stop surface 163. The inner diameter surface 165 of distal clip housing 102 allows for axial transmission of jaw adapter yoke 106, until jaw adapter yoke 106 contacts the hard stop created by distal facing stop surface 163.

With reference to FIGS. 3, 10-11 and 14, the distal portion 138 of the spring release 136 is configured and adapted to be received within the proximal receiving portion 133 of the jaw adapter yoke 106, shown in FIGS. 6-7, to transmit axial and rotational force to the jaw adapter yoke 106. The rotation of drive wire 109 about the longitudinal axis A drives rotation of spring release 136, jaw adaptor yoke 106, distal clip housing 102 and jaw assembly 104 about the longitudinal axis A relative to catheter body 105 and spring tube 142. The distal portion of the spring release 136 is divided into at least two tines 139 and includes a snap feature 141 at the distal most tip of each tine 139. The snap feature 141 includes a tapered outer diameter surface 145 at the distal tip of each tine 139 and a mating surface 156 selectively engageable with an inner surface 135 of the receiving portion 133 of the jaw adapter yoke 106. Each tine includes flat outer surfaces 155 on each side to engage with the square/rectangular inner surfaces 153 of receiving portion 133 to allow torque transmission from drive wire 109 to the distal clip assembly 100. The drive wire 109 is mechanically coupled to a proximal portion 140 of the spring release 136 to transmit linear and rotational motion from the drive wire 109 to the jaw adapter yoke 106. The proximal portion 140 of the spring release 136 being the portion proximal relative to tines 139. The spring release 136 includes a receiving bore 162 opening in the proximal direction for receiving and coupling the drive wire 109 to the spring release 136. The spring release 136 includes an outwardly extending flange portion 152 and an outwardly projecting stop flange 154 positioned proximal to the outwardly extending flange portion 152.

As shown in FIGS. 2-3 and 12-13, the cantilever arms 146 of the spring tube 142 can be laser cut or stamped from the tube body, creating at least one cantilever arm 146. Each cantilever arm 146 includes an inwardly extending flange 158 that removably engages with a circumferential slot 148 defined about a periphery of a proximal end 151 of the distal clip housing 102. The inwardly extending flange 158 is a 90-degree tab bent inwards that mates with corresponding circumferential slot 148 of jaw housing. The spring release 136 is positioned at least partially within the spring tube 142. The spring tube 142 includes inwardly extending v-shaped flange portion 150, e.g., a first formed feature, and inner stop flanges 137, e.g., stop tabs.

Figure 17:
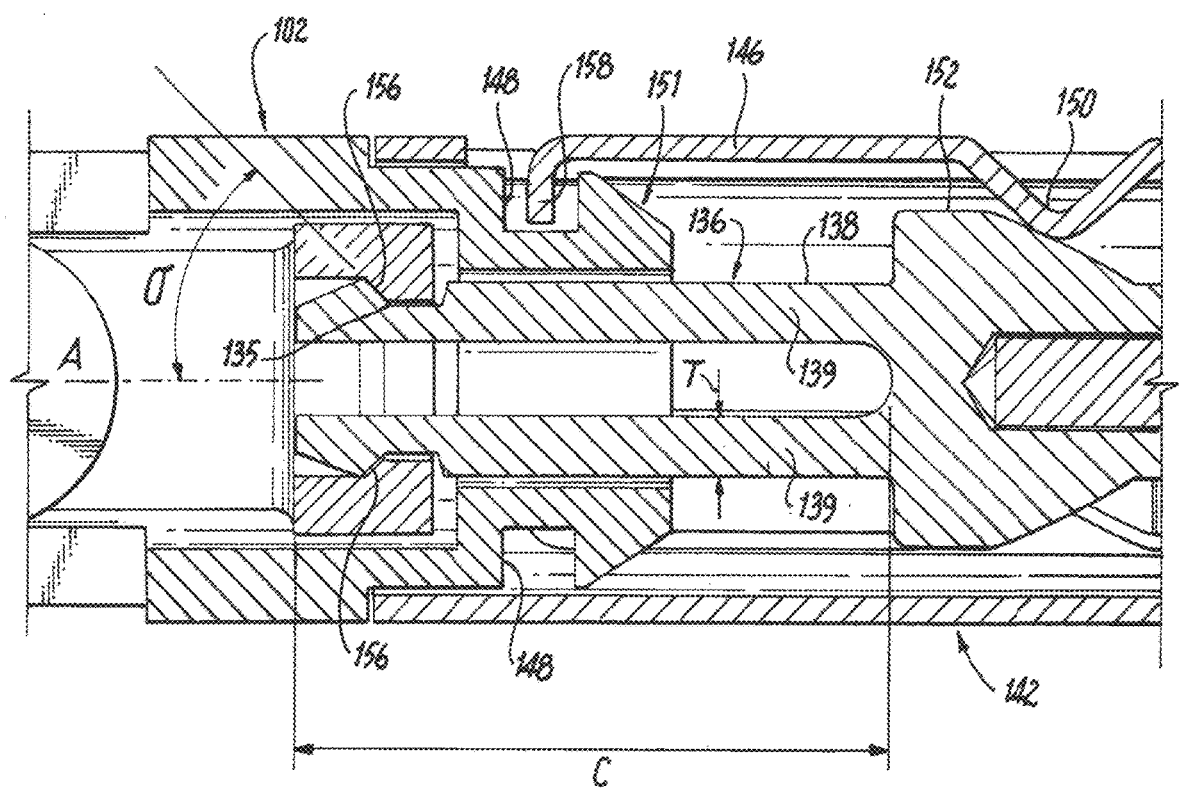
FIG. 17 is a cross-sectional side elevation detail view of a portion of the device of FIG. 1, showing the engagement between the spring release and the jaw adapter yoke and between the spring tube and the distal clip housing before firing.

With reference now to FIGS. 14-17, some of the various configurations of device 10 are shown. In Fig. the In FIG. 15, the device 10 is in a closed configuration and the second pin 118 is translated in a more proximal position within each cam slot 122 relative to the open configuration, but second pin 118 is still distal of the locking neck 130 and the protrusion 131. In the closed configuration, the respective distal tips 124 of the jaw members 108 are approximated towards one another to grasp tissue 15 (but not necessarily in abutment with one another). In FIGS. 16-17, the device 10 is in a locked configuration and the second pin 118 is in a proximal position relative to the locking necks 130 and their respective protrusions 131. In the locked configuration, the second pin 118 is within the proximal locking area 132 of each cam slot 122.

As shown in FIGS. 17-20, once the second pin 118 is in the proximal locking area 132, further axial movement of the spring release 136 in a proximal direction (e.g. away from the tissue 15) acts to "fire" the distal clip assembly 100 by releasing the distal clip assembly 100 from the proximal delivery catheter 101. The further linear motion of the spring release 136 in the proximal direction puts the spring release 136 in tension against jaw adapter yoke 106 due to abutment between mating surface 156 of the snap feature 141 and the inner surface 135 of the receiving portion 133. This tension causes each tine 139 to act as a spring and deflect inwardly, shown schematically by the inwardly pointing arrows in FIG. 19, and release from the receiving portion 133. The release force required to detach spring release 136 from the adapter yoke 106 can be tuned by adjusting the length C of each tine 139, the thickness T of each tine 139, and/or the angle σ of mating surface relative to the longitudinal axis A, show in FIG. 17. The angle σ of mating surface can range from 30 to 60 degrees, preferably being 45 degrees. The ratio of length C to thickness T can range from 8:1 to 10:1, e.g., 9:1. These dimensions provide the desired elastic behavior to ensure consistent release.

With continued reference to FIGS. 17-21, as the spring release 136 moves proximally relative to the jaw adapter yoke 106, it also moves proximally relative to the spring tube 142, thereby causing abutment between an inner diameter surface of the v-shaped flange portions 150 of the cantilever arms 146 of a spring tube 142 with an outwardly extending flange portion 152 of the spring release 136. The abutting causes each cantilever arm 146 to deflect radially outward and disengage the inwardly extending flanges 158 from the circumferential slot 148 at the proximal end 151 of the distal clip housing 102. The outwardly projecting stop flange 154 is configured and adapted to engage with the inner stop flange 137 of spring tube 142 to stop spring release 136 from receding proximally into the catheter body 105. Full disengagement (e.g. "firing") of the distal clip assembly 100 is realized through both the inward deflection of the tines 139 of spring release 136 and the outward deflection of the cantilever arms 146 of spring tube 142.

Figure 21:
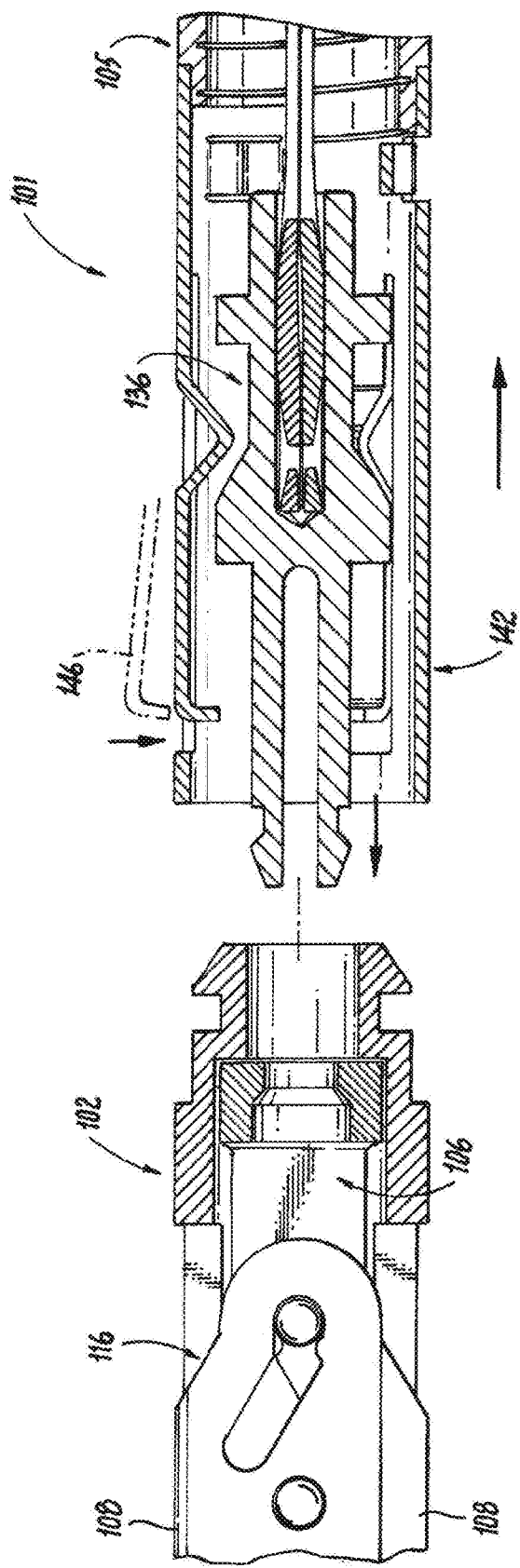
FIG. 21 is a cross-sectional side elevation view of a portion of the device of FIG. 1, showing the spring tube and spring release disconnected from the distal clip assembly for removal of the proximal delivery catheter.

With continued reference to FIGS. 17-21, a single spring component, spring release 136, disengages two springs (tines 139 and cantilever arms 146) simultaneously generating an improved disconnect mechanism that enhances the ability to reposition the clip assembly 100 prior to deployment by simplifying the feedback to the user into a single tactile signal. It also makes accidental deployment of the clip assembly 100 less likely, as fewer components are used to realize disengagement. Because there are fewer components, less space is needed in the distal clip assembly 100, allowing for a shorter clip body. The shorter clip "stem" or overall length of deployed clip relative to jaw size is seen as an improvement. Additionally, the firing mechanism is elastic, and permanent deformation, e.g. breakage, is not required to deploy the clip assembly 100. As such, deployment can be reversible in some embodiments to a certain extent, which allows for the possibility of a multi-use delivery catheter. As shown in FIG. 21, after firing, proximal delivery catheter 101 can then be removed from the surgical site, leaving the distal clip assembly 100 to function as a short-term implant.

A method for firing a hemostatic clip assembly, e.g. distal clip assembly 100, includes positioning the distal clip assembly proximate to a target location, e.g. near tissue 15 as shown in FIG. 14, and translating an actuation portion, e.g. actuation portion 115, of a proximal handle assembly, e.g. proximal handle assembly 103, of a proximal delivery catheter, e.g. proximal delivery catheter 101, relative to a grasping portion, e.g. grasping portion 107, of the proximal handle assembly in at least one of a proximal direction or a distal direction. The actuation portion is operatively connected to a jaw adapter yoke, e.g. jaw adapter yoke 106, via a drive wire, e.g. drive wire 109, and a spring release, e.g. spring release 136 to transmit linear motion to the jaw adapter yoke. The linear motion of the jaw adapter yoke transmits the linear motion to a second pin, e.g. second pin 118, positioned within a cam slot, e.g. cam slot 122, of at least one jaw member, e.g. jaw members 108, thereby rotating at least one of the jaw members about the first pin between an open configuration and a closed configuration.

Figure 18:
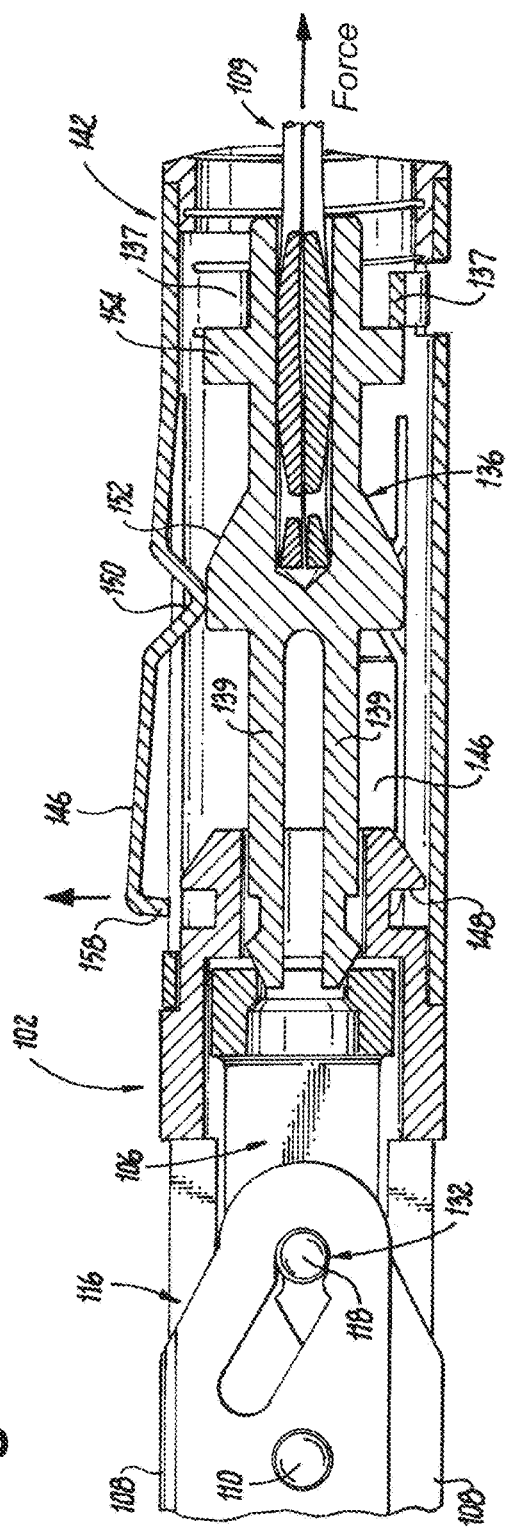
FIG. 18 is a cross-sectional side elevation detail view of a portion of the device of FIG. 1, showing the release of the spring release from the jaw adapter yoke and the release of the spring tube from the distal clip housing when firing the device.
Figure 20:
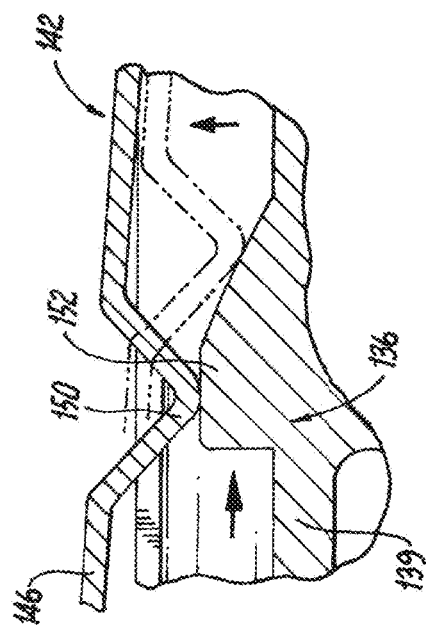
FIG. 20 is a cross-sectional side elevation detail view of a portion of the device of FIG. 1, schematically showing the outward deflection of the cantilever arm of the spring tube as the spring release moves proximally relative to the spring tube when firing the device.
Figure 19:
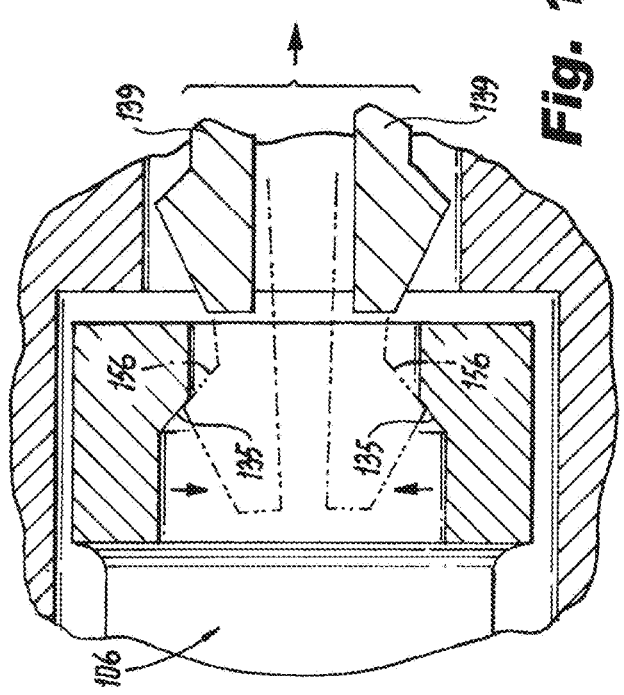
FIG. 19 is a cross-sectional side elevation detail view of a portion of the device of FIG. 1, schematically showing the inward deflection of the tines of the spring release as they move proximally relative to the jaw adapter yoke when firing the device.

The method includes translating the actuation portion in the proximal direction to transmit the linear motion in the proximal direction to the second pin, as shown in FIG. 15, to lock the second pin, as shown behind a lock protrusion, e.g. lock protrusion 131, of the cam slot to lock at least one of the jaw members in a locked configuration, as shown in FIG. 16. Translating the actuation portion includes translating the actuation portion further in the proximal direction to transmit further linear motion in the proximal direction to the spring release, as shown in FIG. 18. The further linear motion in a proximal direction de-coupling a distal portion, e.g. distal portion 138, of the spring release from a receiving portion, e.g., receiving portion 133, of the jaw adapter yoke, as shown in FIG. 21.

Figure 25:
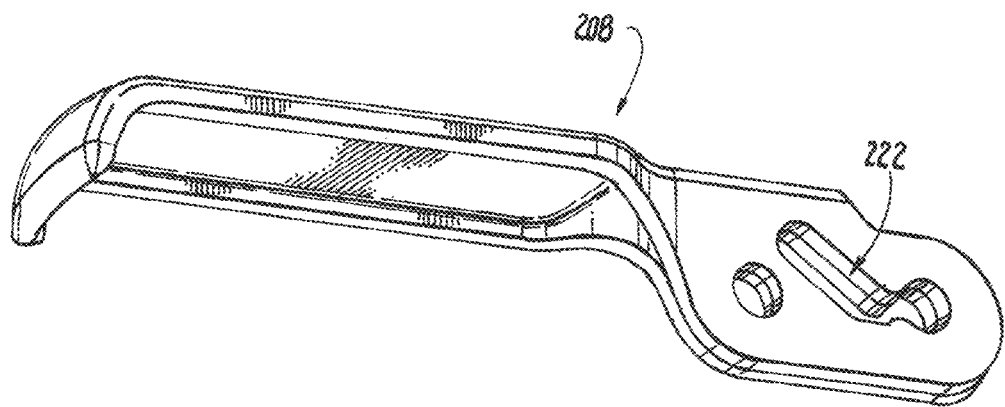
FIG. 25 is a perspective view of another embodiment of a jaw member for use with the device for applying a hemostatic clip assembly of FIG. 1, showing a cam slot.
Figure 26:
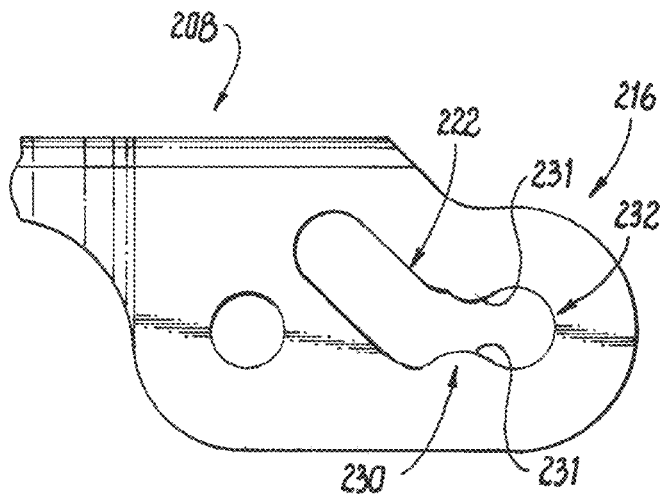
FIG. 26 is a side elevation view of the jaw member of FIG. 25, showing two protrusions in the cam slot.

Referring now to FIGS. 25-29, several different embodiments for the jaw members are described. In FIG. 25-26, an embodiment of a jaw member 208 is shown. Jaw member 208 is similar to jaw members 108 in that it can be used in the jaw assembly 104 and the distal clip assembly 100. Jaw member 208 also includes a distal end effector 220 similar to distal end effector 120. The main difference between jaw member 208 and jaw member 108 is that jaw member 208 includes a cam slot 222 in a proximal portion 216 of the jaw member 208 where the cam slot 222 includes a proximal locking neck 230 with two protrusions 231 projecting into the cam slot 222 defining a proximal locking area 232. Protrusions 231, e.g., detents, interfere with the outer diameter of the of a cam pin, e.g., pin 118. For jaw member 208, the continued axial translation of cam pin 118 forces a widening of the cam slot 222 in an elastic manner and creates an additional resistance force on the internal drivetrain, e.g., spring release 136 and spring tube 142. Once the cam pin 118 crests the inflection point on the protrusions 231, it will snap into place behind the protrusion 231, effectively locking the jaws in a closed position. Because a drive wire, e.g., drive wire 109, operatively connected to jaw member 208 can only transmit limited compression, a user will not be able to translate sufficient force from a handle assembly, e.g., handle assembly 103, distally to move cam pin 118 out of locking area 132 relative to the protrusions 231 to "unlock" the cam pin.

Figure 27:
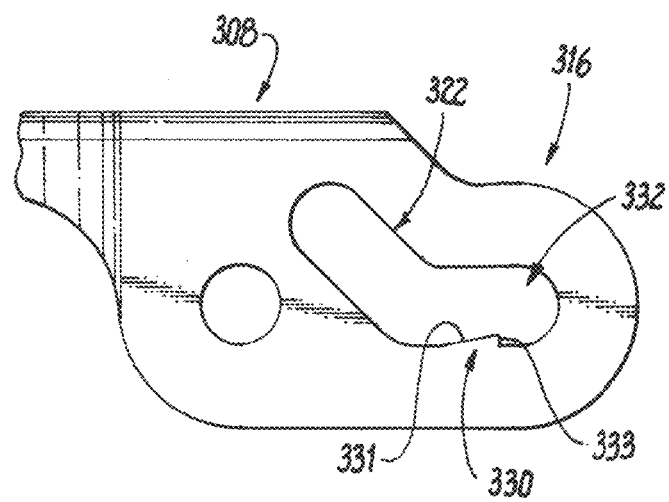
FIG. 27 is a side elevation view of another embodiment of a jaw member for use with the device for applying a hemostatic clip assembly of FIG. 1, showing a tapered portion and a lip in the cam slot.

As shown in FIG. 27, another embodiment of a jaw member 308 is shown. Jaw member 308 is similar to jaw members 108 in that it can be used in the jaw assembly 104 and the distal clip assembly 100. Jaw member 308 also includes a distal end effector similar to distal end effector 120. The main difference between jaw member 308 and jaw member 108 is that jaw member 308 includes a cam slot 322 in a proximal portion 316 of the jaw member 308 having a locking neck 330 formed by a tapered portion 331, e.g., a triangular ramp, having a lip 333. A proximal locking area 332, similar to locking area 132, is defined by the locking neck 330 proximally from the lip 333. This geometry allows an easier transmission of axial force to normal force on the internal walls of cam slot 322, requiring less force to initiate locking. The lip 333 positioned distally relative to the proximal locking area 332 will also prevent axial movement of a cam pin, e.g., cam pin 118, after locking is achieved.

Figure 28:
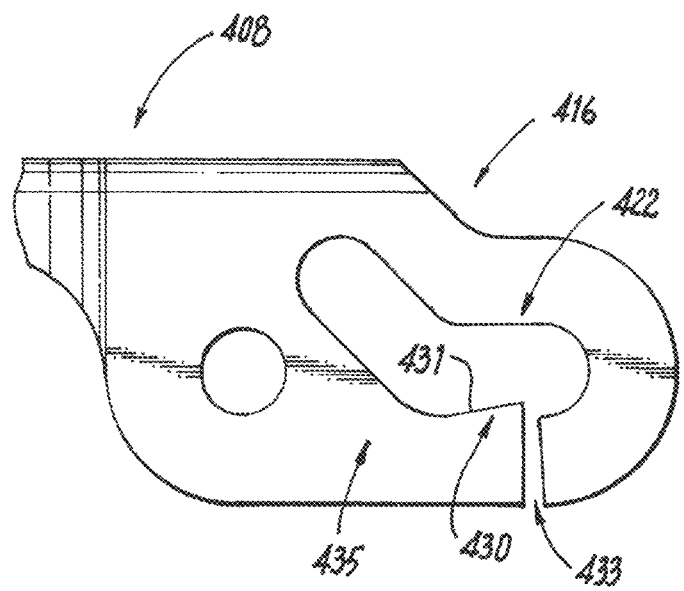
FIG. 28 is a side elevation view of another embodiment of a jaw member for use with the device for applying a hemostatic clip assembly of FIG. 1, showing a slot in the jaw member.

With reference now to FIG. 28, another embodiment of a jaw member 408 is shown. Jaw member 408 is similar to jaw members 108 in that it can be used in the jaw assembly 104 and the distal clip assembly 100. Jaw member 408 also includes a distal end effector similar to distal end effector 120. The main difference between jaw member 408 and jaw member 108 is that jaw member 408 includes a cam slot 422 in a proximal portion 416 of the jaw member 408 having a locking neck 430 formed by a tapered portion 431, e.g., a triangular ramp, terminating in a slot 433. This open contour creates a cantilever lock arm 435 on the bottom wall of cam slot 422. This results in a decreased force required to lock the clip, and results in a higher rate of successful locking in instances where the jaw members 408 are not perfectly parallel to each other, as deflection in the cantilever lock arm 435 can accommodate some axis offset of the jaw members 108. A proximal locking area 432, similar to locking area 132, is defined by the locking neck 430 and positioned proximally from the tapered portion 431.

Figure 29:
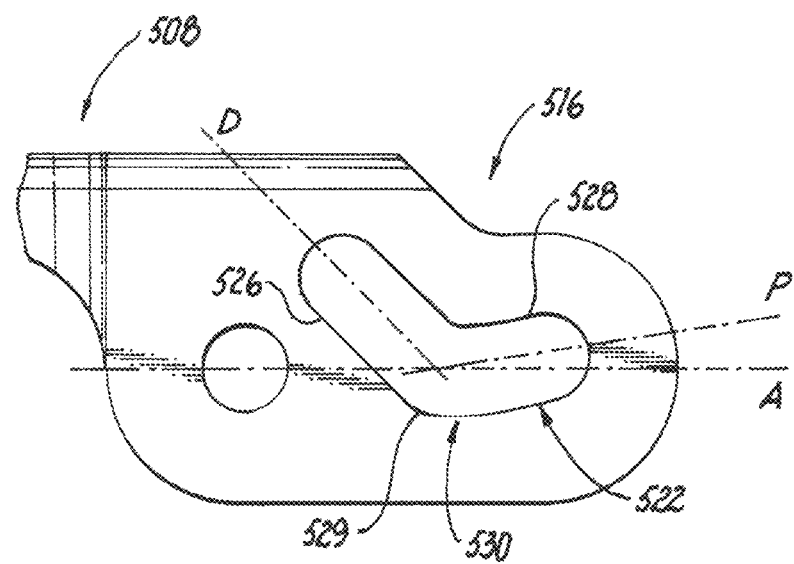
FIG. 29 is a side elevation view of another embodiment of a jaw member for use with the device for applying a hemostatic clip assembly of FIG. 1, showing a reverse slope in the proximal portion of the cam slot.

As shown in FIG. 29, another embodiment of a jaw member 508 is shown. Jaw member 508 is similar to jaw member 108 in that it can be used in the jaw assembly 104 and the distal clip assembly 100. Jaw member 508 also includes a distal end effector similar to distal end effector 120. The main difference between jaw member 508 and jaw member 108 is that jaw member 508 includes a cam slot 522 in a proximal portion 516 of the jaw member 508 having a locking neck 530 formed by a slope reversal on a proximal portion 528 of the cam slot 522. In other words, instead of a proximal axis P of proximal portion 528 being parallel to a longitudinal axis A of a catheter body, e.g., catheter body 105, proximal axis P is angled radially outward relative to axis A resulting in a locking force due to cantilever deflection. In this instance, the user will feel a gradual increase in feedback force, and then a sudden decrease. Once a cam pin, e.g., second pin 118, has crested an inflection point 529 of the pin track (again, relative to the longitudinal axis of the clip body, which is parallel to longitudinal axis A of catheter body at rest) the slope direction changes and begins to force the clip open ever so slightly (0-10 degrees of angulation between jaws. Subsequent unlocking of the jaw members 508 would require equal distal movement of the cam pin relative to a pivot pin, e.g., first pin 110, which is prevented by the spring force required to pass the cam pin over the inflection point during distal translation. Again, an elongate drive wire, e.g., drive wire 109, will not be able to transmit sufficient compressive force to actuate the cam pin distally, effectively locking the clip. The cam slot 522 of jaw member 508 has the as the added benefit of accommodating some amount of tissue thickness between the jaw members 508 without incurring bending stress in the jaw members 508.

Figure 22:
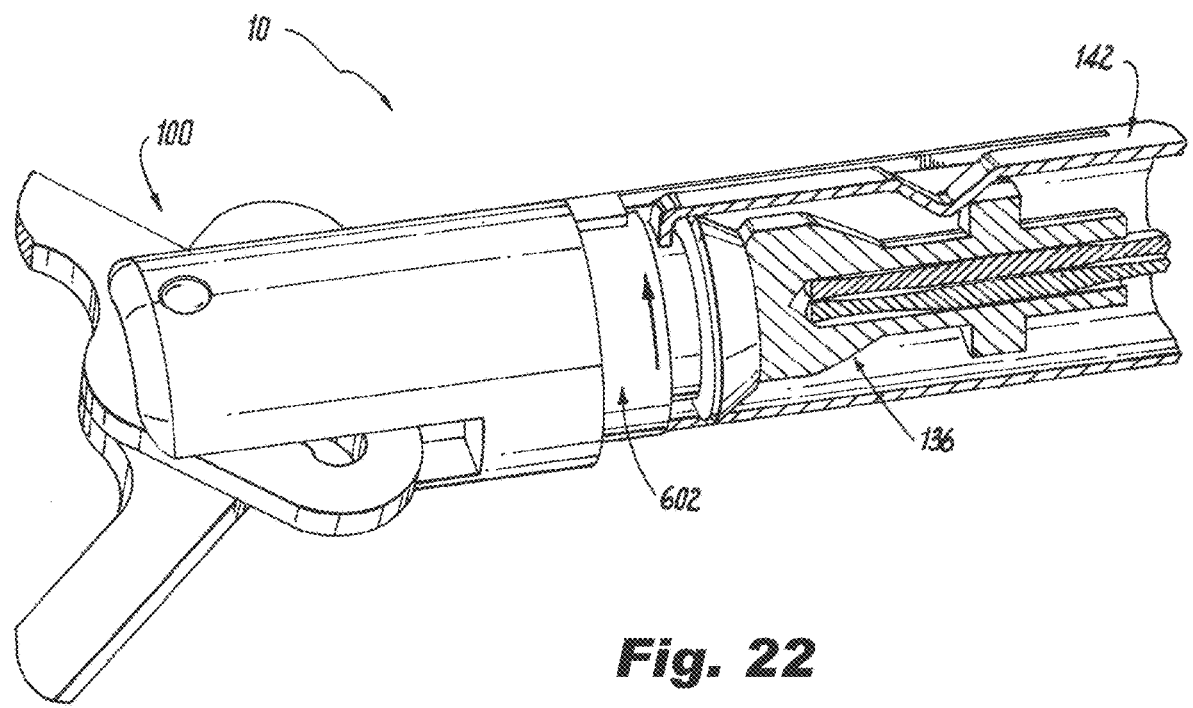
FIG. 22 is a perspective view of a portion of a device for applying a hemostatic clip assembly constructed in accordance with another embodiment of the present disclosure, schematically showing the distal clip housing is rotatable along with the spring release.
Figure 23:
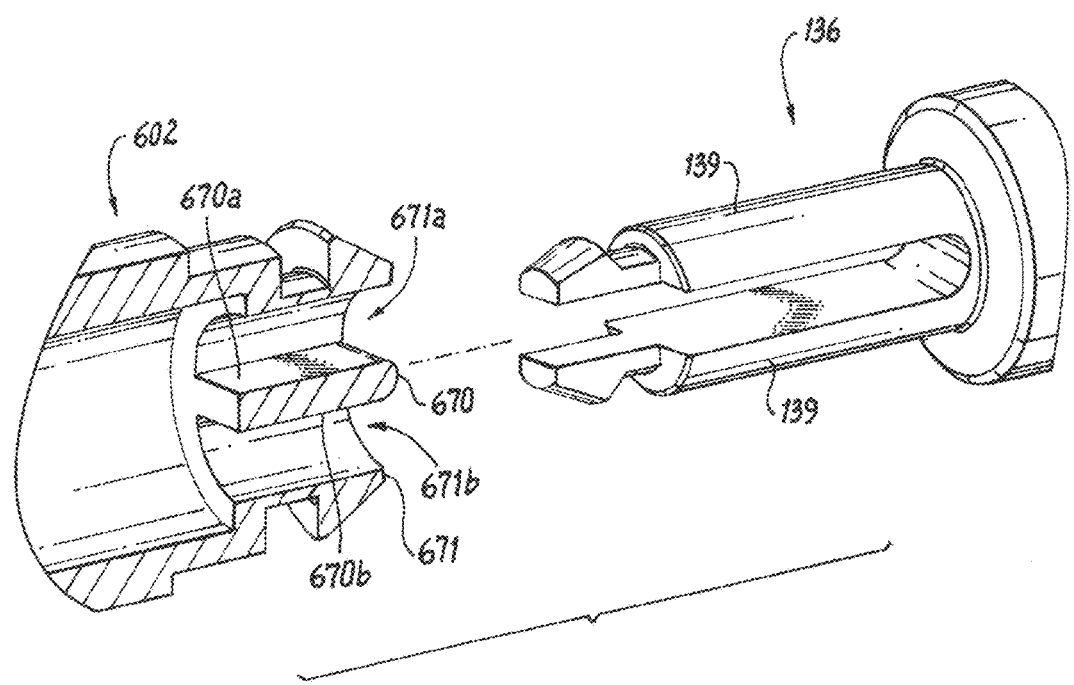
FIG. 23 is a cross-sectional perspective view of the distal clip housing of FIG. 22, showing the distal clip housing including a diametrical center bar to engage with tines of the spring release for rotation'

As shown in FIGS. 22-23, an alternate mechanism for torque transmission in device 10 is proposed where a distal clip housing 602 includes a diametrical center bar 670 extended across opening 671 generating two slots 671a and 671b on either side with two flat surfaces 670a and 670b on the inside of the through hole. These parallel flat surfaces 670a and 670b contact the internal flat edges 168 of tines 139 of spring release 136, shown in FIG. 10, that are formed from a slot between tines 139. The remaining portions of distal clip housing 602 are the same as distal clip housing 102. Distal clip housing 602 can be used in lieu of distal clip housing 102 in device 10. Moreover, when using distal clip housing 602 in device 10, jaw adapter yoke 106 can have a circular proximal receiving portion 133 (instead of rectangular/square), as the torque does not need to be transmitted via the flats 155 on the spring release 136 to the receiving portion 133.

Figure 24:
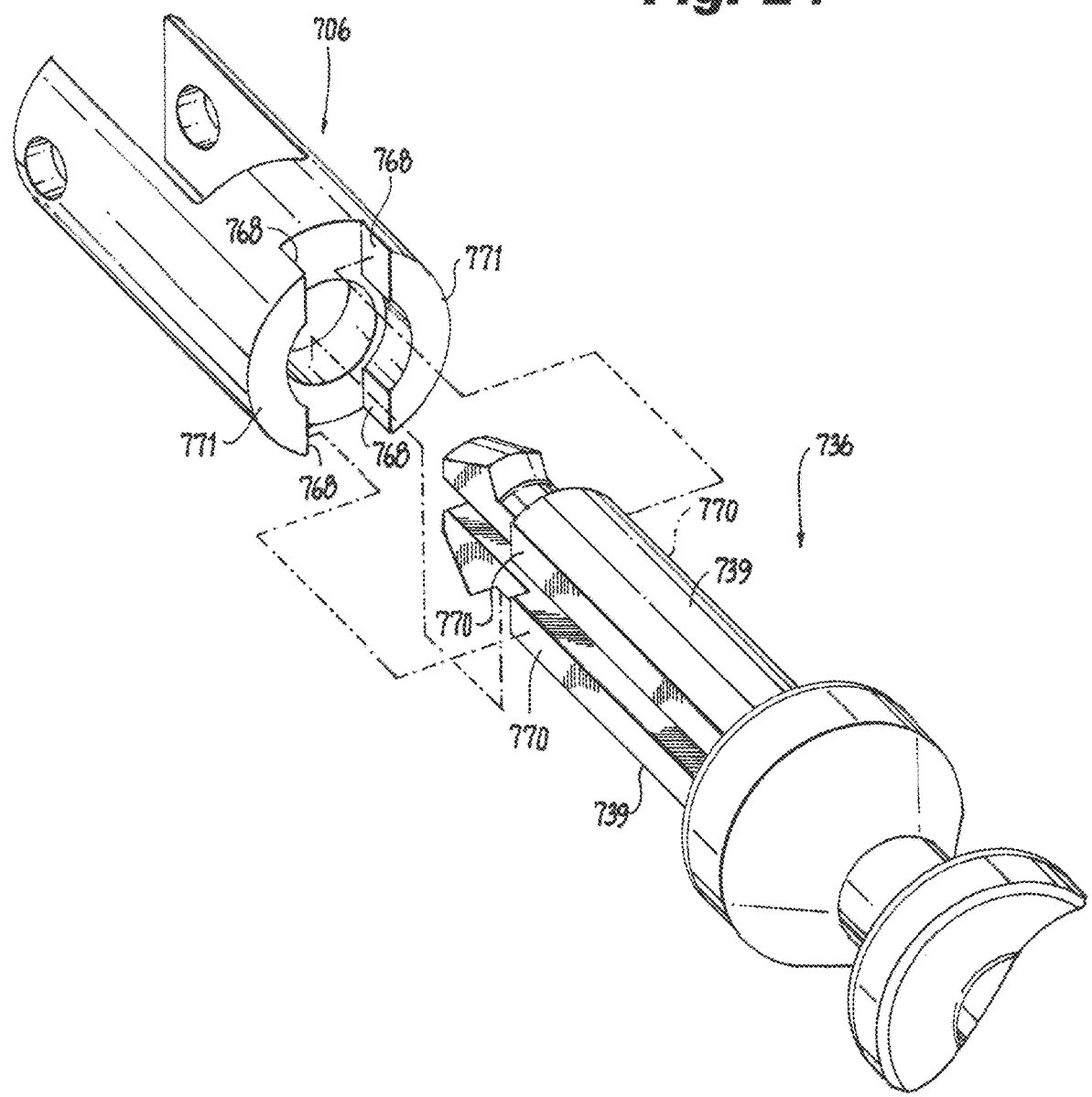
FIG. 24 is a perspective view of portions of another embodiment of a release pin and another embodiment of a jaw adapter yoke constructed in accordance with the present disclosure, showing the jaw adapter yoke having flat bosses extending from a proximal end to engage with flat outer surfaces on tines of the spring release.

As shown in FIG. 24, another alternate mechanism for torque transmission in device 10 is proposed through the connection between alternative embodiments of a spring release 736 and a jaw adapter yoke 706. Spring release 736 is the same as spring release 136 except instead of an arcuate outer surface like that on tines 139, tines 739 include flat portions 770 to abut bosses 771 having flat surfaces 768 extending from the proximal end of the jaw adapter yoke 706 that interface with the aforementioned flat portions 770 of tines 739. Jaw adapter yoke 706 is the same as jaw adapter yoke 106 except for the bosses 771. Spring release 736 and jaw adapter yoke 706 can be used in device 10 in lieu of spring release 136 and jaw adapter yoke 106.

The methods and systems of the present disclosure, as described above and shown in the drawings, provide for a surgical device with superior properties including simplified user feedback, reduced accidental deployment of the clip assembly and a shorter clip body. Additionally, the firing mechanism is elastic, and permanent deformation, e.g., breakage, is not required to deploy the clip assembly. While the apparatus and methods of the subject disclosure have been showing and described with reference to embodiments, those skilled in the art will readily appreciate that changes and/or modifications may be made thereto without departing from the spirit and score of the subject disclosure.

What is claimed is:

1. A device for applying a hemostatic clip assembly, the device comprising:
   a proximal delivery catheter including a proximal handle assembly and an elongated catheter body extending distally from the proximal handle assembly, the elongated catheter body defining a longitudinal axis; and
   a distal clip assembly removably connected to a distal end of the elongated catheter body, the distal clip assembly including a distal clip housing, a jaw assembly having a pair of cooperating jaw members fixed to the distal clip housing by a first pin, the first pin oriented orthogonally relative to the longitudinal axis, and a jaw adapter yoke operatively connected to the jaw members, wherein the proximal delivery catheter is configured and adapted to transmit linear motion along the longitudinal axis and torsion about the longitudinal axis to at least a portion of the distal clip assembly, wherein at least one of the jaw members is configured and adapted to rotate about the first pin between an open configuration and a closed configuration
   wherein the distal clip assembly includes a second pin connecting between the jaw members and the jaw adapter yoke, wherein each jaw member includes a proximal body portion and a distal end effector, wherein the proximal body portion of each jaw member includes a respective cam slot configured and adapted to receive the second pin and a pivot aperture configured and adapted to receive the first pin,
   wherein the second pin is configured and adapted to translate within the cam slots to move axially relative to the distal clip housing and the jaw assembly to move the jaw members between the open configuration where respective distal tips of the jaw members are moved away from one another, the closed configuration where the respective distal tips of the jaw members are approximated towards one another to grasp tissue, and a locked configuration, and
   wherein each cam slot includes a proximal locking neck projecting into the cam slot defining a proximal locking area, wherein the jaw members are in the locked configuration when the second pin is proximal relative to the proximal locking neck in the proximal locking area.

2. The device as recited in claim 1, wherein the distal clip housing includes a pair of spaced apart arms defining a slot configured and adapted to provide clearance for respective proximal portions of the jaw members to rotate relative the first pin.

3. The device as recited in claim 1, wherein each cam slot defines a distal portion and a proximal portion, wherein the distal portion of each cam slot is angled relative to the proximal portion of each cam slot.

4. The device as recited in claim 3, wherein the proximal portion of each cam slot defines a proximal axis extending in a first direction, the distal portion of each cam slot defines a distal axis extending at an oblique angle relative to the proximal axis, and the distal axes of each cam slot are positioned at opposite angles relative to one another.

5. The device as recited in claim 1, wherein the proximal locking neck includes at least one of a protrusion projecting into the cam slot or a tapered portion.

6. A device for applying a hemostatic clip assembly, the device comprising:
   a proximal delivery catheter including a proximal handle assembly and an elongated catheter body extending distally from the proximal handle assembly, the elongated catheter body defining a longitudinal axis; and
   a distal clip assembly removably connected to a distal end of the elongated catheter body. the distal clip assembly including a distal clip housing, a jaw assembly having a pair of cooperating jaw members fixed to the distal clip housing by a first pin, the first pin oriented orthogonally relative to the longitudinal axis, and a jaw adapter yoke operatively connected to the jaw members, wherein the proximal delivery catheter is configured and adapted to transmit linear motion along the longitudinal axis and torsion about the longitudinal axis to at least a portion of the distal clip assembly, wherein at least one of the jaw members is configured and adapted to rotate about the first pin between an open configuration and a closed configuration, wherein the jaw adapter yoke includes a proximal receiving portion and the proximal delivery catheter includes a spring release having a distal portion configured and adapted to be received within the proximal receiving portion of the jaw adapter yoke to transmit axial and rotational force to the jaw adapter yoke.

7. The device as recited in claim 6, wherein the proximal delivery catheter includes a drive wire coupled to a proximal portion of the spring release to transmit linear and rotational motion from the drive wire to the jaw adapter yoke.

8. The device as recited in claim 7, wherein the proximal handle assembly includes an actuation portion coupled to a proximal end of the drive wire, and a grasping portion, wherein the actuation portion is configured and adapted to translate relative to the grasping portion to apply axial force to the drive wire.

9. The device as recited in claim 6, wherein the distal clip housing includes a pair of spaced apart arms defining a slot configured and adapted to provide clearance for respective proximal portions of the jaw members to rotate relative the first pin.

10. A device for applying a hemostatic clip assembly, the device comprising:
a proximal delivery catheter including a proximal handle assembly and an elongated catheter body extending distally from the proximal handle assembly, the elongated catheter body defining a longitudinal axis; and
a distal clip assembly removably connected to a distal end of the elongated catheter body, the distal clip assembly including a distal clip housing, a jaw assembly having a pair of cooperating jaw members fixed to the distal clip housing by a first pin, the first pin oriented orthogonally relative to the longitudinal axis, and a jaw adapter yoke operatively connected to the jaw members, wherein the proximal delivery catheter is configured and adapted to transmit linear motion along the longitudinal axis and torsion about the longitudinal axis to at least a portion of the distal clip assembly, wherein at least one of the jaw members is configured and adapted to rotate about the first pin between an open configuration and a closed configuration, wherein the proximal delivery catheter includes a spring tube between a proximal end of the distal clip assembly and a distal end of the catheter body, wherein the spring tube includes at least one cantilever arm removably coupled to the distal clip housing, wherein the at least one cantilever arm includes an inwardly extending flange that removably engages with a circumferential slot defined about a periphery of a proximal end of the distal clip housing, and wherein the proximal delivery catheter includes a spring release positioned at least partially within the spring tube, wherein the spring tube includes an inwardly extending flange portion, wherein the spring release includes an outwardly extending flange portion configured and adapted to interact with the inwardly extending flange portion of the spring tube to selectively deflect the at least one cantilever arm of the spring tube and release the inwardly extending flange of the at least one cantilever arm from the circumferential slot of the distal clip housing.

11. The device as recited in claim 10, wherein the spring release includes a distal portion configured and adapted to be received within a receiving portion of the jaw adapter yoke to transmit linear and rotational motion to the jaw adapter yoke.

12. The device as recited in claim 11, wherein the distal portion of the spring release is divided into at least two tines, wherein each tine has a mating surface selectively engageable with an inner surface of the receiving portion of the jaw adapter yoke.

13. The device as recited in claim 12, wherein each tine is configured and adapted to deflect inwardly and release from the receiving portion when an axial force in a proximal direction is applied to the spring release.

14. The device as recited in claim 10, wherein the distal clip housing includes a pair of spaced apart arms defining a slot configured and adapted to provide clearance for respective proximal portions of the jaw members to rotate relative the first pin.

* * * * *